(12) United States Patent
Klosterman et al.

(10) Patent No.: US 7,904,167 B2
(45) Date of Patent: Mar. 8, 2011

(54) TELEMETRY SYSTEM FOR USE WITH MICROSTIMULATOR

(75) Inventors: Daniel J. Klosterman, Valencia, CA (US); Kelly H. McClure, Simi Valley, CA (US); Goran N. Marnfeldt, Valencia, CA (US); Jordi Parramon, Valencia, CA (US); Matthew I. Haller, Valley Village, CA (US); Rudolph V. Park, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1075 days.

(21) Appl. No.: 11/624,364

(22) Filed: Jan. 18, 2007

(65) Prior Publication Data

US 2007/0135867 A1 Jun. 14, 2007

Related U.S. Application Data

(62) Division of application No. 10/607,962, filed on Jun. 27, 2003, now Pat. No. 7,177,698.

(60) Provisional application No. 60/392,475, filed on Jun. 28, 2002.

(51) Int. Cl.
*A61N 1/00* (2006.01)
(52) U.S. Cl. ............................................. 607/60; 607/61
(58) Field of Classification Search .............. 607/31–33, 607/60–61
See application file for complete search history.

(56) References Cited

U.S. PATENT DOCUMENTS

| | | |
|---|---|---|
| 2,800,616 A | 7/1957 | Becker |
| 3,288,641 A | 11/1966 | Rightmire |
| 4,134,408 A | 1/1979 | Brownlee et al. |
| 4,441,498 A | 4/1984 | Nordling |
| 4,561,443 A | 12/1985 | Hogrefe et al. |
| 5,193,539 A | 3/1993 | Schulman et al. |
| 5,193,540 A | 3/1993 | Schulman et al. |
| 5,312,439 A | 5/1994 | Loeb |

(Continued)

FOREIGN PATENT DOCUMENTS

WO 97/18857 A1 5/1997

(Continued)

OTHER PUBLICATIONS

U.S. Appl. No. 10/133,766, filed Apr. 26, 2006, Parramon et al.

(Continued)

*Primary Examiner* — Mark W Bockelman
(74) *Attorney, Agent, or Firm* — Wong, Cabello, Lutsch, Rutherford & Brucculeri, LLP

(57) ABSTRACT

An implantable microstimulator configured to be implanted beneath a patient's skin for tissue stimulation employs a bi-directional RF telemetry link for allowing data-containing signals to be sent to and from the implantable microstimulator from at least two external devices. Further, a separate electromagnetic inductive telemetry link allows data containing signals to be sent to the implantable microstimulator from at least one of the two external devices. The RF bidirectional telemetry link allows the microstimulator to inform the patient or clinician regarding the status of the microstimulator device, including the charge level of a power source, and stimulation parameter states. The microstimulator has a cylindrical hermetically sealed case having a length no greater than about 27 mm and a diameter no greater than about 3.3 mm. A reference electrode is located on one end of the case and an active electrode is located on the other end of the case.

13 Claims, 32 Drawing Sheets

U.S. PATENT DOCUMENTS

| | | | |
|---|---|---|---|
| 5,372,605 A | 12/1994 | Adams et al. | |
| 5,405,367 A | 4/1995 | Schulman et al. | |
| 5,571,148 A | 11/1996 | Loeb et al. | |
| 5,642,030 A | 6/1997 | Seelye | |
| 5,733,313 A * | 3/1998 | Barreras et al. | 607/33 |
| 5,750,926 A | 5/1998 | Schulman et al. | |
| 5,769,877 A | 6/1998 | Barreras, Sr. | |
| 5,807,397 A | 9/1998 | Barreras | |
| 5,861,019 A | 1/1999 | Sun et al. | |
| 5,951,594 A | 9/1999 | Kerverm | |
| 6,051,017 A | 4/2000 | Loeb et al. | |
| 6,061,596 A | 5/2000 | Richmond et al. | |
| 6,073,050 A | 6/2000 | Griffith | |
| 6,131,581 A | 10/2000 | Leysieffer et al. | |
| 6,148,235 A | 11/2000 | Kuiper | |
| 6,164,284 A | 12/2000 | Schulman et al. | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,195,585 B1 | 2/2001 | Karunasiri et al. | |
| 6,208,894 B1 | 3/2001 | Schulman et al. | |
| 6,212,430 B1 | 4/2001 | Kung | |
| 6,214,032 B1 | 4/2001 | Loeb et al. | |
| 6,240,316 B1 | 5/2001 | Richmond et al. | |
| 6,259,937 B1 | 7/2001 | Schulman et al. | |
| 6,280,873 B1 | 8/2001 | Tsukamoto | |
| 6,315,721 B2 | 11/2001 | Schulman et al. | |
| 6,366,817 B1 | 4/2002 | Kung | |
| 6,400,991 B1 | 6/2002 | Kung | |
| 6,424,867 B1 | 7/2002 | Snell et al. | |
| 6,458,171 B1 | 10/2002 | Tsukamoto | |
| 6,516,227 B1 | 2/2003 | Meadows et al. | |
| 6,553,263 B1 | 4/2003 | Meadows et al. | |
| 6,561,975 B1 * | 5/2003 | Pool et al. | 600/300 |
| 6,567,703 B1 | 5/2003 | Thompson et al. | |
| 6,582,441 B1 | 6/2003 | He et al. | |
| 6,605,382 B2 | 8/2003 | Ruth et al. | |
| 6,607,843 B2 | 8/2003 | Ruth et al. | |
| 6,631,296 B1 | 10/2003 | Parramon et al. | |
| 6,826,430 B2 | 11/2004 | Faltys et al. | |
| 6,920,359 B2 | 7/2005 | Meadows et al. | |
| 2001/0053476 A1 | 12/2001 | Ruth et al. | |
| 2002/0055779 A1 | 5/2002 | Andrews | |
| 2002/0161403 A1 * | 10/2002 | Meadows et al. | 607/1 |
| 2003/0078634 A1 | 4/2003 | Schulman et al. | |
| 2003/0171787 A1 | 9/2003 | Money et al. | |
| 2005/0021108 A1 | 1/2005 | Klosterman et al. | |

FOREIGN PATENT DOCUMENTS

| | | |
|---|---|---|
| WO | 00/01320 A3 | 1/2000 |
| WO | 01/60450 | 8/2001 |
| WO | 01/82398 A1 | 11/2001 |
| WO | 02/09808 | 2/2002 |
| WO | 03/005465 | 1/2003 |

OTHER PUBLICATIONS

U.S. Appl. No. 60/748,240, filed Dec. 7, 2005, He et al.

Cameron, et al., "Micromodular Implants to Provide Electrical Stimulation of Paralyzed Muscles and Limbs," IEEE Transactions on Biomedical Engineering, vol. 44, No. 9, (Sep. 1997), pp. 781-790.

Loeb, et al., "North Sea: Transducers and Electrodes- Injectable Microstimulator for Functional Electrical Stimulation," Med. & Biol. Eng. & Computer, North Sea Special Feature, (Nov. 29, 1991), pp. NS13-NS19.

Loeb, et al., "BION™ Bionic Neurons for Functional and Therapeutic Electrical Stimulation," 20th Annual International Conference of IEEE Engineering in Medicine and Biology "Biomedical Engineering Towards the Year 2000 and Beyond," Oct. 29-Nov. 1, 1998, Hong Kong, 5 pages.

* cited by examiner

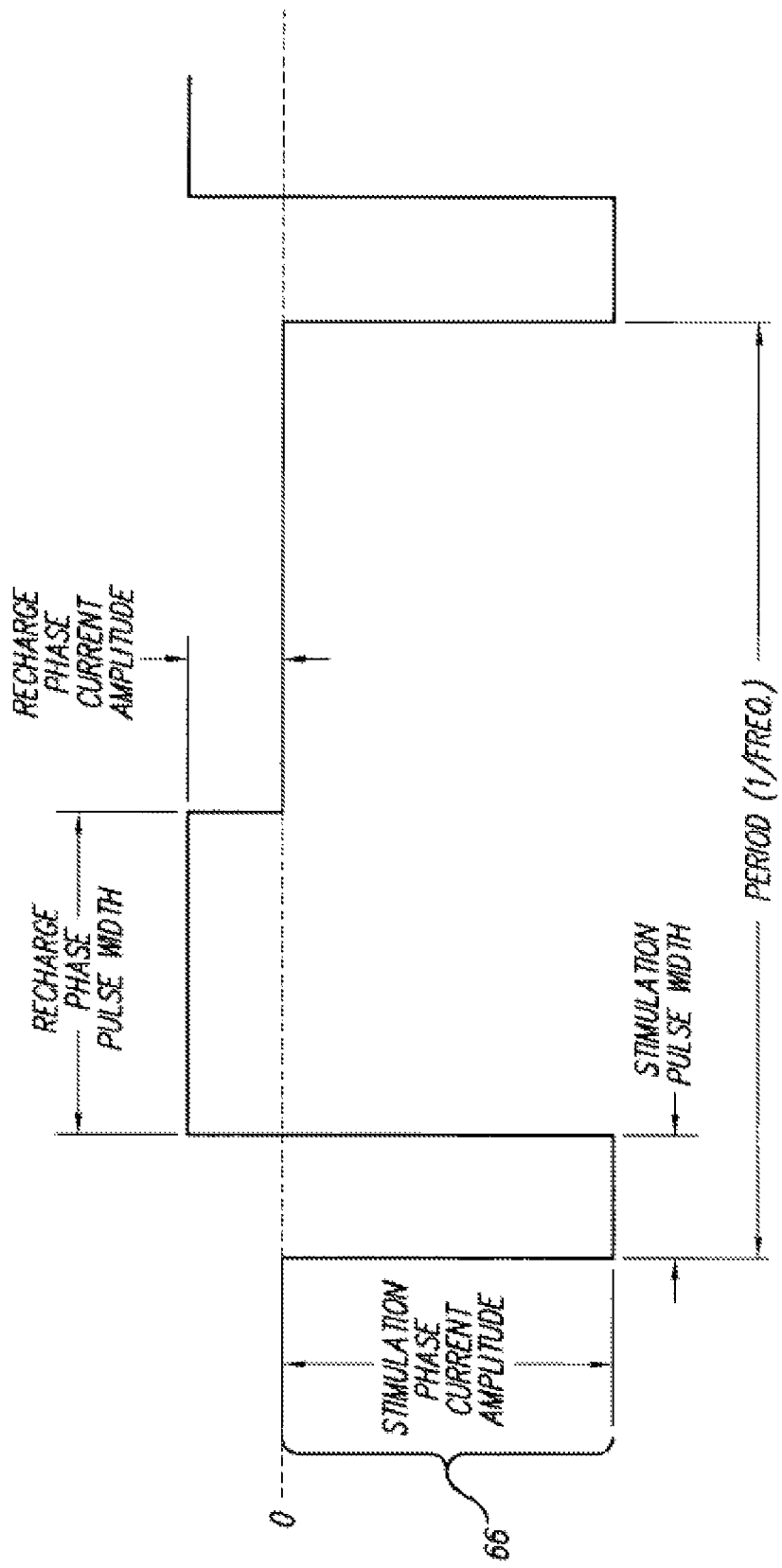

FIG. 3-1

| | STIMULATION PARAMETERS | | | | |
|---|---|---|---|---|---|
| PULSE PARAMETER | MINIMUM VALUE | MAXIMUM VALUE | INCREMENT | TOLERANCE | DEFAULT VALUE |
| STIMULATION ENABLE | DISABLED | ENABLED | N/A | N/A | DISABLED |
| STIMULATION AMPLITUDE | 0 mA | 10.0 mA | 0.2 mA | GREATER OF ±0.05 mA AND ±10% | 0.0 mA |
| BRB RECHARGE AMPLITUDE | 0 μA | 620 μA | 20 μA | GREATER OF ±10μA AND ±20% | 0 μA |
| PULSE WIDTH | 50 μsec | 1550 μsec | 50 μsec | ±10% | 50 μsec |
| PULSE FREQUENCY (LOW RANGE) | 0 pps | 50 pps | 1.0 pps | GREATER OF ±12% OR 0.6pps | 0 pps |
| PULSE FREQUENCY (LOW MID-RANGE) | 55 pps | 225 pps | 5 pps | ±12% | 0 pps |
| PULSE FREQUENCY (HIGH MID-RANGE) | 250 pps | 550 pps | 25 pps | ±12% | 0 pps |
| PULSE FREQUENCY (HIGH RANGE) | 625 pps | 1125 pps | 100 pps | ±12% | 0 pps |
| RAMP ON STEP SIZE | 0.05 mA | 0.4 mA | 2x | ±10% | 0.05 mA |
| BURST MODE ENABLE | DISABLED | ENABLED | N/A | N/A | DISABLED |

| STIMULATION PARAMETERS | | | | | |
|---|---|---|---|---|---|
| PULSE PARAMETER | MINIMUM VALUE | MAXIMUM VALUE | INCREMENT | TOLERANCE | DEFAULT VALUE |
| ... | ... | ... | ... | ... | ... |
| BURST MODE "ON" TIME (SHORT RANGE) | 0 sec | 25.8 sec | 0.41 sec | ±10% | 0 sec |
| BURST MODE "ON" TIME (MID RANGE) | 26.4 sec | 416 sec (6.93 min) | 6.6 sec | ±10% | 0 sec |
| BURST MODE "ON" TIME (LONG RANGE) | 420 sec | 6,615 sec (1.84 hr) | 105 sec | ±10% | 0 sec |
| BURST MODE "OFF" TIME (SHORT RANGE) | 0 sec | 25.8 sec | 0.41 sec | ±10% | 0 sec |
| BURST MODE "OFF" TIME (MID RANGE) | 26.4 sec | 416 sec (6.93 min) | 6.6 sec | ±10% | 0 sec |
| BURST MODE "OFF" TIME (LONG RANGE) | 420 sec | 6,615 sec (1.84 hr) | 105 sec | ±10% | 0 sec |
| PATIENT MIN. AMPLITUDE (REGISTER: NOT USED DURING STIMULATION) | 0.2 mA | PATIENT MAX. AMPLITUDE | 0.2 mA | N/A | 0.2 mA |
| PATIENT MAX AMPLITUDE (REGISTER: NOT USED DURING STIMULATION) | PATIENT MIN. AMPLITUDE | 10.0 mA | 0.2 mA | N/A | 0.2 mA |
| ... | ... | ... | ... | ... | ... |

FIG. 3-2

TELEMETRY SYSTEM FOR USE WITH MICROSTIMULATOR

CROSS-REFERENCE TO RELATED APPLICATIONS

This application is a divisional application of U.S. patent application Ser. No. 10/607,962, filed Jun. 27, 2003, which in turn was based on U.S. Provisional Patent Application Ser. No. 60/392,475, filed Jun. 28, 2002. Priority is claimed to these earlier applications, and each are incorporated herein by reference in their entireties.

FIELD OF THE INVENTION

The present invention relates generally to the field of implantable medical devices and more particularly to microstimulator devices incorporating a telemetry system that allows communications to occur between the implanted microstimulator and one or more external (non-implanted) devices.

BACKGROUND

Implantable microstimulators, also known as BION devices (where BION is a registered trademark of Advanced Bionics Corporation, of Sylmar, Calif.), are typically characterized by a small, cylindrical housing which contains electronic circuitry that produces electric currents between spaced electrodes. These microstimulators are implanted proximate to target tissue, and the currents produced by the electrodes stimulate the tissue to reduce symptoms or otherwise provide therapy for various disorders. An implantable battery-powered medical device may be used to provide therapy for various purposes including nerve or muscle stimulation. For example, urinary urge incontinence may be treated by stimulating the nerve fibers proximal to the pudendal nerves of the pelvic floor; erectile or other sexual dysfunctions may be treated by providing stimulation of the cavernous nerve(s); and other disorders, e.g., neurological disorders caused by injury or stroke, may be treated by providing stimulation of other appropriate nerve(s).

Implantable microstimulators have been disclosed that provide therapy for neurological disorders by stimulating the surrounding nerves or muscles. Such devices are characterized by a sealed housing which contains electronic circuitry for producing electric currents between spaced electrodes. A microstimulator is precisely implanted proximate to the target tissue area and the electrical currents produced at the electrodes stimulate the tissue to reduce the symptoms and otherwise provide therapy for the neurological disorder.

A battery-powered microstimulator of the present invention is preferably of the type referred to as a BION device, which may operate independently, or in a coordinated manner with other implanted devices, or with external devices.

By way of example, in U.S. Pat. No. 5,312,439, entitled Implantable Device Having an Electrolytic Storage Electrode, an implantable device for tissue stimulation is described. U.S. Pat. No. 5,312,439 is incorporated herein by reference. The described microstimulator shown in the '439 patent relates to an implantable device using one or more exposed, electrolytic electrodes to store electrical energy received by the implanted device, for the purpose of providing electrical energy to at least a portion of the internal electrical circuitry of the implantable device. It uses an electrolytic capacitor electrode to store electrical energy in the electrode when exposed to body fluids.

Another microstimulator known in the art is described in U.S. Pat. No. 5,193,539, "Implantable Microstimulator," which patent is also incorporated herein by reference. The '539 patent describes a microstimulator in which power and information for operating the microstimulator is received through a modulated, alternating magnetic field in which a coil is adapted to function as the secondary winding of a transformer. The induction coil receives energy from outside the body and a capacitor is used to store electrical energy which is released to the microstimulator's exposed electrodes under the control of electronic control circuitry.

In U.S. Pat. Nos. 5,193,540 and 5,405,367, which patents are incorporated herein by reference, a structure and method of manufacture of an implantable microstimulator is disclosed. The microstimulator has a structure which is manufactured to be substantially encapsulated within a hermetically-sealed housing inert to body fluids, and of a size and shape capable of implantation in a living body, with appropriate surgical tools. Within the microstimulator, an induction coil receives energy from outside the body requiring an external power supply.

In yet another example, U.S. Pat. No. 6,185,452, which patent is likewise incorporated herein by reference, there is disclosed a device configured for implantation beneath a patient's skin for the purpose of nerve or muscle stimulation and/or parameter monitoring and/or data communication. Such a device contains a power source for powering the internal electronic circuitry. Such power supply is a battery that may be externally charged each day. Similar battery specifications are found in U.S. Pat. No. 6,315,721, which patent is additionally incorporated herein by reference.

Other microstimulator systems prevent and/or treat various disorders associated with prolonged inactivity, confinement or immobilization of one or more muscles. Such microstimulators are taught, e.g., in U.S. Pat. No. 6,061,596 (Method for Conditioning Pelvis Musculature Using an Implanted Microstimulator); U.S. Pat. No. 6,051,017 (Implantable Microstimulator and Systems Employing the Same); U.S. Pat. No. 6,175,764 (Implantable Microstimulator System for Producing Repeatable Patterns of Electrical Stimulation; U.S. Pat. No. 6,181,965 (Implantable Microstimulator System for Prevention of Disorders); U.S. Pat. No. 6,185,455 (Methods of Reducing the Incidence of Medical Complications Using Implantable Microstimulators); and U.S. Pat. No. 6,214,032 (System for Implanting a Microstimulator). The applications described in these additional patents, including the power charging techniques, may also be used with the present invention. The '596, '017, '764, '965, '455, and '032 patents are incorporated herein by reference.

It is also known in the art to use thermal energy to power an at least partially implantable device, as taught in U.S. Pat. No. 6,131,581, also incorporated herein by reference, wherein an implantable thermoelectric energy converter is disclosed.

Despite the various types of microstimulators known in the art, as illustrated by the examples cited above, significant improvements are still possible and desirable, particularly relative to a microstimulator having a bi-directional telemetry system that allows communications with the microstimulator once implanted, coupled with a self-contained primary or rechargeable battery that: (a) accommodates the various needs of a microstimulator; (b) accommodates various locations in the implanted site; (c) allows the microstimulator to operate longer between charges or replacement, and/or (d) allows better and easier control and/or monitoring of the implanted microstimulator.

SUMMARY OF THE INVENTION

The present invention addresses the above and other needs by providing a battery-powered microstimulator intended to provide therapy for neurological disorders such as urinary urge incontinence by way of electrical stimulation of nerve fibers in the pudendal nerve; to treat various disorders associated with prolonged inactivity, confinement, or immobilization of one or more muscles; to be used as therapy for erectile dysfunction and other sexual dysfunction; as a therapy to treat chronic pain; and/or to prevent or treat a variety of other disorders. The invention disclosed and claimed herein provides such a battery-powered microstimulator and associated external components.

Stimulation and control parameters of the implanted microstimulator are preferably adjusted to levels that are safe and efficacious with minimal discomfort. Different stimulation parameters have different effects on neural tissue, and parameters may be chosen to target specific neural populations and to exclude others. For example, relatively low frequency neurostimulation (i.e., less than about 50-100 Hz) may have an excitatory effect on surrounding neural tissue, leading to increased neural activity, whereas relatively high frequency neurostimulation (i.e., greater than about 50-100 Hz) may have an inhibitory effect, leading to decreased neural activity.

In accordance with certain embodiments of the invention, there is provided a microstimulator sized to contain a self-contained power source, e.g., a primary battery. In another embodiment, the self-contained power source comprises a battery which is rechargeable by an external power source, e.g., an RF link, an inductive link, or other energy-coupling link. In yet other embodiments, the power source may comprise other energy sources, such as a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is placed in the middle of the long, thin-rod shape of the microstimulator), a bioenergy power source (where a chemical reaction provides an energy source), a fuel cell (much like a battery, but does not run down or require recharging, but requires only a fuel), a bioelectrical cell (where two or more electrodes use tissue-generated potentials and currents to capture energy and convert it to useable power), an osmotic pressure pump (where mechanical energy is generated due to fluid ingress), or the like.

For purposes of the present invention, the term "self contained" means implanted within the patient and not totally dependent upon external (non implanted) sources of energy. Typically, the self contained power source will be contained within a housing, e.g., the same housing as the one that contains the electronic circuits of the implantable device, that is implanted within the patient or user of the device. A key feature of the self contained power source is that it is not dependent upon a continuous source of external (non-implanted) power. The self-contained power source used with the invention may rely upon an occasional use of an external power source, e.g., an occasional burst or infrequent injection of energy to replenish the self contained power source, such as a rechargeable battery or super capacitor, but the "self contained" power source may thereafter operate on its own to provide needed power for operation of the device without being connected or coupled to the external source of power.

In accordance with various embodiments of the invention, there is provided a microstimulator with at least two electrodes for applying stimulating current to surrounding tissue and associated electronic and/or mechanical components encapsulated in a hermetic package made from biocompatible material. The internal components are powered by the internal power source. The internal power source is, in one preferred embodiment, a primary battery, and in another preferred embodiment, a rechargeable battery. In other embodiments, the energy source may take the form of any of the various energy sources mentioned above, or combinations thereof.

In accordance with one aspect of the invention, there is provided a microstimulator with means for receiving and/or transmitting signals via telemetry at an arm's length distance, e.g., up to two feet. The telemetry system includes means for receiving and/or storing control parameters to operate the microstimulator in a desired manner. Further, the microstimulator is able to transmit data related to the status of the microstimulator, including data sensed through sensors incorporated within, or coupled to, the microstimulator. The telemetry system further allows for receiving and/or storing electrical power within the microstimulator and for receiving and/or transmitting signals indicating the charge level of the internal battery.

In accordance with another aspect of the invention, there is provided a microstimulator implantable via a minimal surgical procedure and the associated surgical tools.

In accordance with a further aspect of the invention, there is provided a method for manufacturing/assembling the components within the microstimulator, including the internal battery or other power source, ferrite material, induction coil, storage capacitor, and other components using e.g., conductive and non-conductive adhesives, are described herein. Also described herein are methods of externally coating the hermetically sealed cylindrical housing to protect the internal components.

It is to be noted that embodiments described herein may include some or all of the items mentioned above. Additional embodiments will be evident upon further review of the present disclosure.

BRIEF DESCRIPTION OF THE DRAWINGS

The above and other aspects of the present invention will be more apparent from the following more particular description thereof, presented in conjunction with the following drawings wherein:

FIG. 2 shows a representative biphasic electrical current stimulation waveform that may be produced by the battery-powered BION system of the present invention;

FIG. 3 shows a table summarizing exemplary battery-powered BION stimulation parameters;

Corresponding reference characters indicate corresponding components throughout the several views of the drawings.

DETAILED DESCRIPTION OF THE INVENTION

Figure 1:
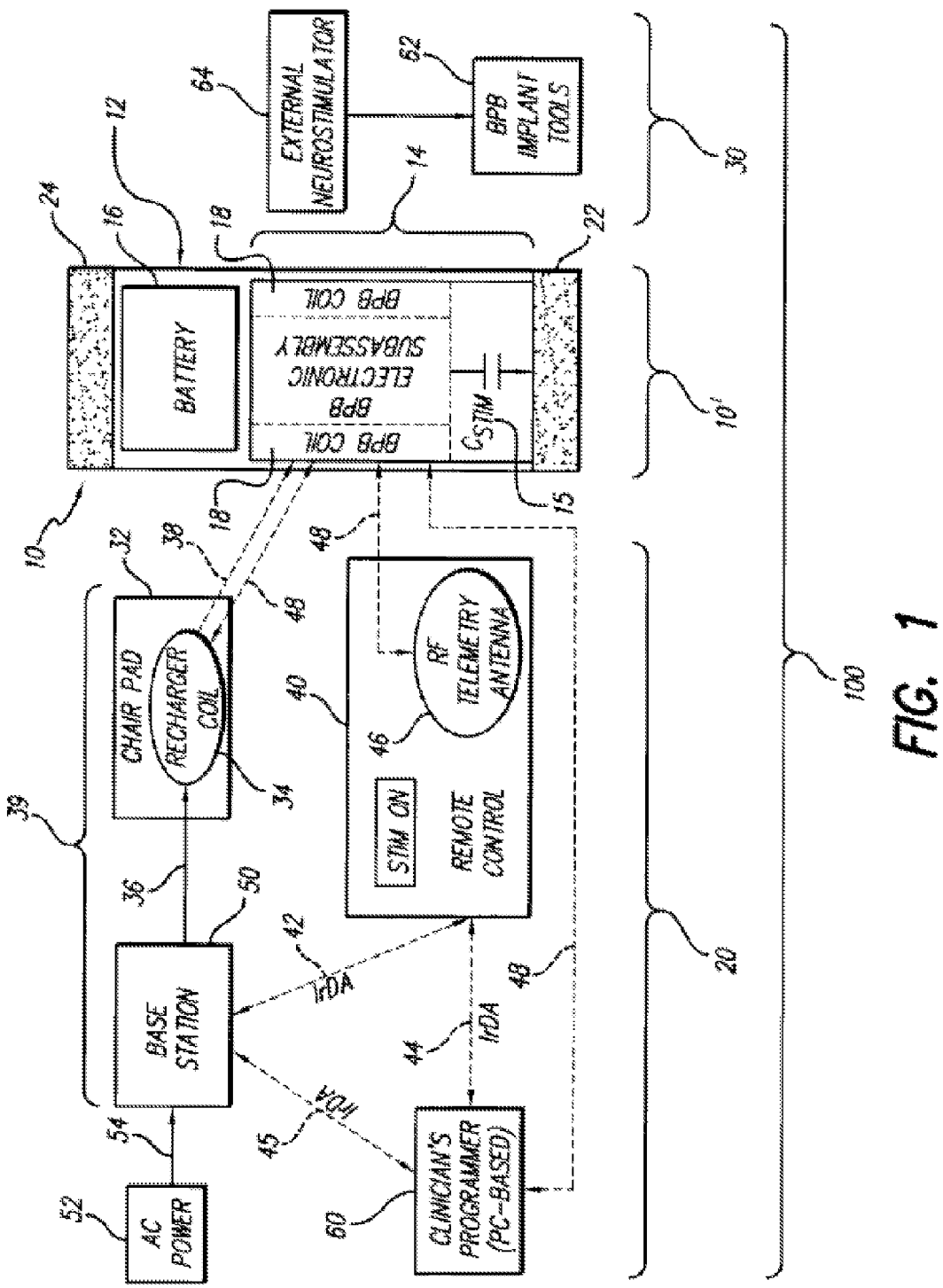
FIG. 1 is a block diagram for an exemplary battery-powered BION (BPB) system made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

A fully assembled battery-powered microstimulator (also referred to as a BION microstimulator, or battery-powered BION ("BPB" device) made in accordance with the present invention may operate independently, or in a coordinated manner with other implanted devices, or with external devices.

The BPB device is a pulse generator which includes an internal power source. Regardless of whether the internal power source comprises a primary battery, a rechargeable battery, or an alternative power source as described below, the device containing the internal power source will be referred to as a BPB device for purposes of the present invention.

In one preferred embodiment, the power source comprises a rechargeable battery. The battery is recharged, as required, from an external battery charging system, typically through an inductive link.

In another preferred embodiment, the power source comprises a primary battery. A primary battery, or primary battery cell, offers the advantage of typically having five to ten times more energy density than does a rechargeable battery. Further, a primary battery typically exhibits a much lower self-leakage than does a rechargeable battery.

In other embodiments of the invention, the power source of the BPB device comprises an alternative energy source, or a combination of alternative energy sources. One such alternative energy source is a super capacitor. A super capacitor typically has ten times less energy density than does a rechargeable battery, but it can be recharged very quickly, thus allowing for the use of a simple combination RC and charger system. Additionally, power coupled inductively to a super capacitor storage element may enable pulsed radio frequency (RF) power to be used, rather than continuous RF power. A super capacitor is typically used, most advantageously, in combination with another power source, such as a primary battery or a rechargeable battery. The super capacitor may be charged rapidly, and then the charge stored on the super capacitor is available to supplement operation of the BPB device, either directly (to assist with higher energy stimulation levels or power requirements), or indirectly (to help recharge the battery).

A further alternative energy source that may be used with the BPB device of the invention is a nuclear battery, also known as an atomic battery. Recent developments have indicated that, e.g., a micro-electro-mechanical system (MEMS) nuclear battery is capable of delivering significant amounts of power. These power sources are extremely small, and may be combined or grouped together, as required, in order to provide the needed power to operate the BPB device.

Still another alternative energy source that may be used with the BPB device is a mechanical resonator. Generating power from mechanical resonators and normal human movement has long been practiced in the art, e.g., with wrist-watches, and MEMS versions of such resonators have been around for a number of years. However, to applicants' knowledge, the use of MEMS mechanical resonators has never been applied to implantable devices, such as the BPB device of the present invention.

A further alternative energy source for use with a BPB device is an infrared collector, or infrared (solar) power source. Because the skin and body tissue is relatively transparent to red and infrared light, it is possible, e.g., through the use of an implanted silicon photovoltaic cell, to collect sufficient energy to power the BPB device from an external infrared source, such as the sun.

Yet an additional alternative energy source for use with the BPB device of the present invention is a thermally-powered energy source. For example, thermal difference engines based on memory shape alloys have been demonstrated to be very efficient engines capable of generating power with minimal temperature differences. Hence, by incorporating such a thermal difference engine within the BPB device, an internal energy source is provided that derives its energy from a small temperature difference, e.g., the temperature difference between the surface of the skin and a location 2-3 cm deeper inside the body.

Still another alternative energy source is a flexural powered energy source. The BPB device has the general shape of a long thin rod. Hence, by placing a flexible section in the middle of the device, such section will be subjected to flexural forces. Such flexural forces, when applied to a suitable piezoelectric element coupled to the flexible section, will generate piezoelectric bimorphs which may be used to generate a voltage (power). Such technique has been used to generate power from wind.

Another alternative energy source is a bioenergy power source. In a bioenergy power source, a chemical reactor interacts with constituents to produce mechanical or electrical power.

A fuel cell represents another type of alternative energy source that may be used with the BPB device. A fuel cell, in principle, operates much like a battery. Unlike a battery, however, a fuel cell does not run down or require recharging. Rather, it produces energy in the form of electricity and heat as long as fuel is supplied. A fuel cell system which includes a "fuel reformer" can utilize the hydrogen from any hydrocarbon fuel. Several fuel cell technologies may be used with the BPB device of the present invention, such as Phosphoric Acid, Proton Exchange Membrane or Solid Polymer, Molten Carbonate, Solid Oxide, Alkaline, Direct Methanol, Regenerative, Zinc Air, or Protonic Ceramic. Such fuel cells may be designed for a single use, or refillable.

Yet an additional alternative energy source that may be used with the BPB device is a bioelectrical cell. In a bioelectrical cell, a set of electrodes (two or more) is implanted in the body tissue. These electrodes sense and use tissue generated potentials and currents in order to power the BPB device. Tissue such as cardiac muscle, cardiac conducting cells and neural tissue are examples of ussue that generates electrical potentials and currents. In a particular case, specialized biological tissue may be implanted to provide the energy. The implanted biological tissue remains alive due to the environment provided by the body where it is implanted.

A further alternative energy source that may be used with the BPB device of the present invention is an osmotic pressure pump. Osmotic pressure pumps may be used to generate mechanical energy due to water, or other fluid, ingress. This mechanical energy may then be used to generate other forms of energy, such as electrical energy. For example, osmotic pressure may be used to separate the plates of a capacitor. As the plates of the capacitor separate with a given amount of charge due to osmotic pressure, the energy stored in that capacitor is incremented.

In the description of the BPB device that follows, the power source used within the BPB device is described as a rechargeable battery. However, it is to be understood, as previously indicated, that the "power source" used within the BPB device may take many forms, including a primary battery or the alternative power sources enumerated above, and that when the term "battery" or "power source" is used herein, such terms, unless otherwise indicated, are meant to broadly convey a source of energy or power contained within, or coupled to, the BPB device.

The BPB device is a fully integrated, programmable, autonomous microstimulator. The key features of the BPB device are that: (1) it is fully integrated, i.e., the BPB device is self contained (electrodes, power source, single channel stimulator), and no attachments are needed; (2) it is programmable, i.e., external devices, such as a remote control, base station, or clinician's programmer, may command the BPB device to perform different functions, such as stimulation, communication, or state; (3) it is autonomous, i.e., the BPB device may operate independently; and (4) it is small—micro-sized small, having typical dimensions that are 27 mm long, 3.3 mm diameter, and weighing only about 0.7 grams.

The BPB device preferably has a substantially cylindrical shape, although other shapes are possible, and at least portions of the BPB device are hermetically sealed. The BPB device includes a processor and other electronic circuitry that allow it to generate stimulus pulses that are applied to a patient through electrodes in accordance with a program that may be stored, if necessary or desired, in programmable memory.

The BPB device circuitry, power source capacity, cycle life, hermeticity, and longevity provide implant operation at typical settings for a long time, e.g., at least five years. Battery (or power source) control circuitry protects the battery or other power source from overcharging, if recharging is needed, and operates the BPB device in a safe mode upon energy depletion, and avoids any potentially endangering failure modes, with a zero tolerance for unsafe failure or operational modes. The BPB device accepts programming only from compatible programming devices.

The publications and patents listed in the table below, which are all incorporated herein by reference, describe various uses of the implantable BPB device for the purpose of treating various neurological conditions:

| Application/Patent/ Publication No. | Filing/ Publication Date | Title |
| --- | --- | --- |
| U.S. Pat. No. 6,061,596 | Issued May 9, 2000 | Method for Conditioning Pelvic Musculature Using an Implanted Microstimulator |
| U.S. Pat. No. 5,193,540 | Issued Mar. 16, 1993 | Structure and Method of Manufacture of an Implantable Microstimulator |
| PCT Publication WO 00/01320 | Published Jan. 13, 2000 | Implantable Stimulator System and Method for Treatment of Urinary Incontinence |
| PCT Publication WO 97/18857 | Published May 29, 1997 | System and Method for Conditioning Pelvic Musculature Using an Implanted Microstimulator |

An implantable BPB system made in accordance with the present invention typically includes internal and external components, as well as surgical components, as shown in FIG. 1. The internal components 10' are implanted in the target tissue area of the patient and the external components 20 are used to recharge or replenish (when recharge or replenishment is needed) and communicate with the internal components. The components shown in FIG. 1 represent as a whole an implantable BION microstimulator system 100. It should be noted that the present invention is not directed to a specific method for treating a disorder, but rather describes possible BPB configurations, methods of manufacture, and how the implantable BPB system functions in conjunction with the components shown in FIG. 1.

A block diagram that illustrates the various components of the BPB system 100 is depicted in FIG. 1. These components may be subdivided into three broad categories: (1) implantable components 10', (2) external components 20, and (3) surgical components 30.

Figure 21:
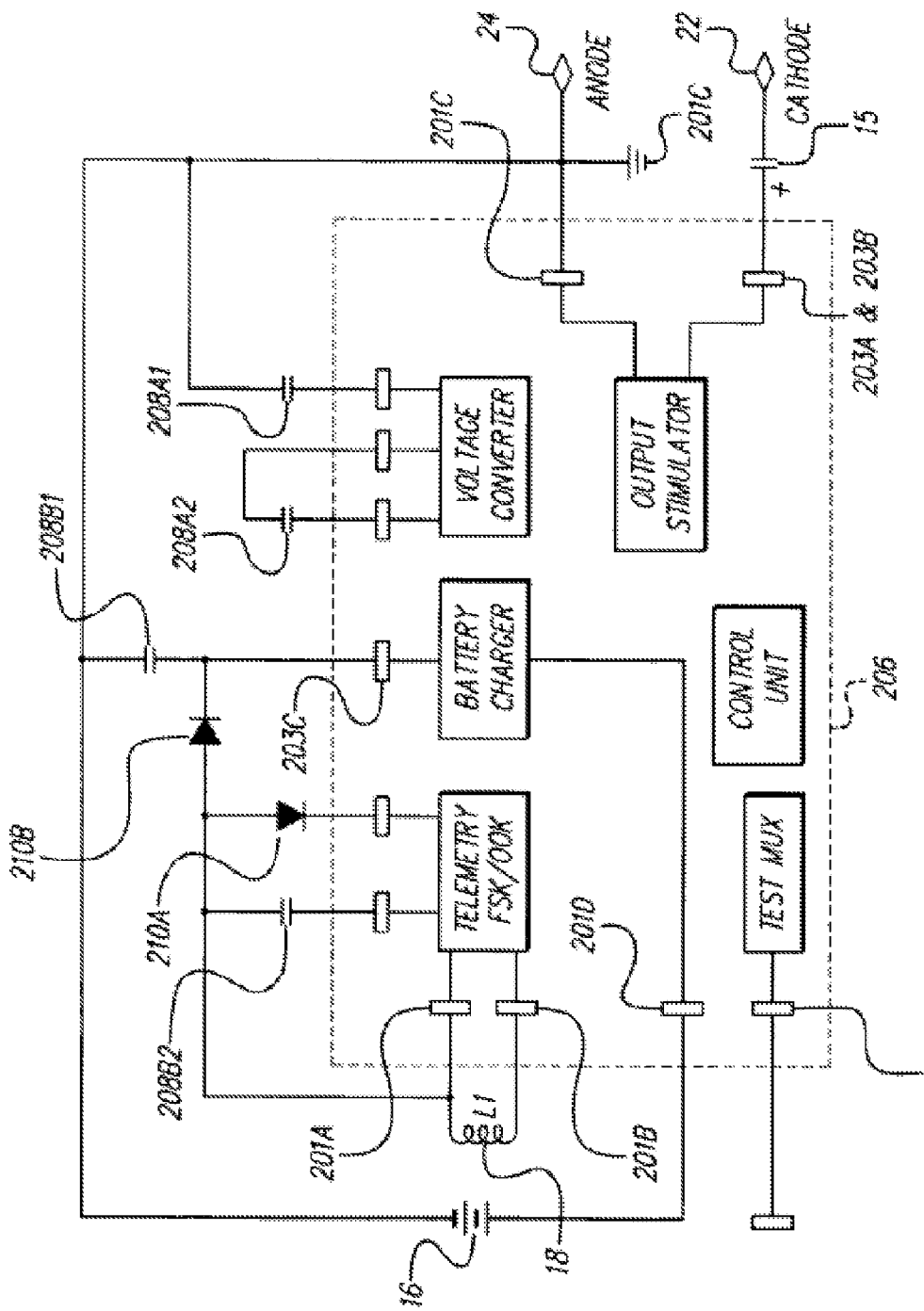
FIG. 21 is an exemplary circuit block diagram showing the main implantable components and their interactions of one embodiment of the invention.

As seen in FIG. 1, the BPB device 10 includes a case 12; battery 16; BPB electronic subassembly 14, which includes BPB coil 18 and a stimulating capacitor $C_{STIM}$ 15; indifferent/reference electrode 24; and active/stimulating electrode 22. The block diagram shown in FIG. 21 also shows the main implantable components of the BPB device 10 and their interactions.

The external components 20, shown in FIG. 1 include charging system 39, which consists of the chair pad 32 and the base station 50; a remote control 40; and a clinician's programmer 60. The chair pad 32 has a recharger coil 34 which is electrically connected to (or may be part of) the base station 50 with extension 36 and communicates with the BPB electronic subassembly 14 with a bidirectional telemetry link 48. The base station 50 has an external medical grade AC adapter which receives AC power 52 through extension 54. The remote control 40 sends and receives communication from/to the base station 50 through Infrared Data Association, IrDA interface 42. (IrDA is a standard for transmitting data via infrared light.) The remote control 40 also communicates with the clinician's programmer 60 through an IrDA interface 44 and communicates with the BPB electronic subassembly 14 with an RF telemetry antenna 46 through the bidirectional telemetry link 48. The clinician's programmer 60 may also communicate with the BPB electronic subassembly 14 through the bidirectional telemetry link 48. The base station 50 also communicates with the clinician's programmer 60 through an IrDA interface 45. The bidirectional telemetry link 48 is also known as the FSK (Frequency Shift Key) telemetry link, or RF telemetry link. In addition, the charging system 39 has a forward telemetry link 38. Such link may use OOK-PWM (On/Off Keying-Pulse Width Modulation), and is typically an inductive telemetry link. When used, both power and information may be transferred to the BPB device through the OOK-PWM link. When charging is not needed, e.g., when the battery comprises a primary battery, such an inductive link may still be used to transfer information and data to the BPB device.

It is thus seen that the OOK-PWM link 38 provides a second means for communicating with the BPB device 10, where the first means comprises the FSK link 48. Having two separate communication channels in this manner adds an additional safety feature to the BION system. One preferred telemetry system that may be used with the BPB device is described more fully below.

The surgical components 30 illustrated in FIG. 1 include the BPB implant tools 62 and an external neurostimulator 64. The implantable BPB device 10 is inserted through the patient's tissue through the use of appropriate surgical tools, and in particular, through the use of tunneling tools, as are known in the art, or as are specially developed for purposes of implantable BPB stimulation systems.

FIG. 1 represents the BPB system 100 as a block diagram which aids in simplifying each of the described implantable components 10', external components 20, and surgical components 30. A better understanding of the possible functions associated with every element of the internal components 10', external components 30, and surgical components 30 is provided in the details that follow.

Turning next to FIG. 2, an exemplary waveform is shown that illustrates some of the BPB biphasic electric current stimulation parameters. Other parameters not shown include burst, ramp, and duty cycles. The BPB device 10 may produce, for instance, an asymmetric biphasic constant-current charge-balanced stimulation pulse, as shown in FIG. 2. Charge-balancing of the current flow through the body tissue in both directions is important to prevent damage to the tissue which results from continued preponderance of current flow in one direction. The first phase of the stimulation pulse is cathodic and the second phase (recharge phase) utilizes an anodic charge recovery to facilitate a charge balance. The stimulation phase current amplitude 66 is programmable from 0.0 to about 10 mA, for instance, in 0.2 mA increments. To prevent patient discomfort due to rapidly increasing or decreasing amplitudes in the first phase of the waveform (of stimulation amplitude 66), changes in amplitude occur smoothly over a transition period programmable by adjusting the allowed slope (step size increments) of the amplitude through continuous pulses.

The stimulation capability of the BPB device 10 is depicted by the stimulation parameters specified in the table shown in FIG. 3. These parameters may be achieved by the electronic subassembly 14, battery (or other power source) 16, and electrodes 22 and 24. The stimulating electrode 22 is coupled to the electronic subassembly 14 with a stimulating capacitor $C_{STIM}$ 15. Net DC charge transferred during stimulation is prevented by the capacitive coupling provided by the stimulating capacitor 15, between the BPB electronic subassembly 14 and the stimulation electrode 22. During the first phase of the pulse waveform shown in FIG. 2, the BPB stimulation electrode 22 has a cathodic polarity with associated negative current amplitude, and the reference electrode 24 is the anode.

Each BPB device 10 has an identification code used to uniquely identify the device. The identification code allows each unit to act on particular messages containing its unique identification code. Each BPB device 10 also responds to universal identification codes used for cases in which the unique address is unknown by the external device, the unique address has been corrupted, or when a command is sent to multiple BPB units.

Referring back to FIG. 1, the BPB device 10 receives commands and data from the remote control 40, clinician's programmer 60, and/or charging system 39 via FSK (frequency shift keying) telemetry link 48. The range of the FSK telemetry link 48 is no less than 30 cm in an optimal orientation. Factors that may affect the range of the FSK telemetry link 48 include an impaired BPB device, depleted external device, insufficient power, environmental noise, and other factors, e.g., the surroundings. When a request is sent to the BPB device 10 by the clinician's programmer 60, the remote control 40, or the charging system 39, the maximum response time for the FSK telemetry link 48 is less than 2 seconds, under normal operating conditions.

The OOK (On-Off Keying) telemetry link 38, shown in FIG. 1, allows commands and data to be sent by the charging system 39 to the BPB device 10. The range of the OOK telemetry link 38 is ideally no less than 15 cm in any orientation and no less than 15 cm in an optimal orientation. The OOK telemetry link 38 allows the charging system 39 to communicate with the BPB device 10 even when the BPB device 10 is not actively listening for a telemetry signal, e.g., when the BPB device 10 is in the Hibernation State or the Storage State (states for the BPB device which will be discussed in detail below). The OOK-PWM telemetry link 38 also provides a communication interface in an emergency situation, e.g., an emergency shutdown.

Reverse telemetry is also available through the FSK telemetry link 48. The reverse FSK telemetry link 48, allows information to be reported by the BPB device 10 to the clinician's programmer 60, the remote control 40, and/or the charging system 39. The range of the reverse telemetry link 48 is no less than 30 cm in an optimal orientation. The type of information transmitted from the BPB device 10 to the clinician's programmer 60, remote control 40, and/or charging system 39, may include but is not limited to battery voltage, BPB internal register settings, and acknowledgments.

The FSK telemetry system, in one preferred embodiment, operates in the frequency band of 127 KHz±8 KHz. When the BPB device 10 has received a valid (i.e. non-error containing) message, an acknowledgment is transmitted.

There will be times when the messages sent in either direction on the telemetry link will not be received by the intended recipient. This may be due to range, orientation, noise, or other problems. The severity of the problem will determine the appropriate response of the system. For example, if a programming change is made by the clinician's programmer 60 and a response is expected by the clinician's programmer 60 from the BPB device 10, the clinician's programmer 60 attempts to get a response from the BPB device 10 until a satisfactory response is received, or until a reasonable number of attempts are made. If no satisfactory response is obtained, this might indicate that the BPB device 10 does not have sufficient power in its internal power source 16 to make a response, in which case charging should be attempted by the user (if the battery 16 is a rechargeable battery). Events such as these are logged for future diagnostic analysis. Error messages are displayed on the clinician' programmer 60, the remote control 40, and/or the base station 50, in response to an abnormal response to telemetry communication. When an invalid command is received by BPB device 10, no action occurs. All valid commands are executed by the BPB device 10 within 1 second after receiving a command, under normal operating conditions.

Figure 22:
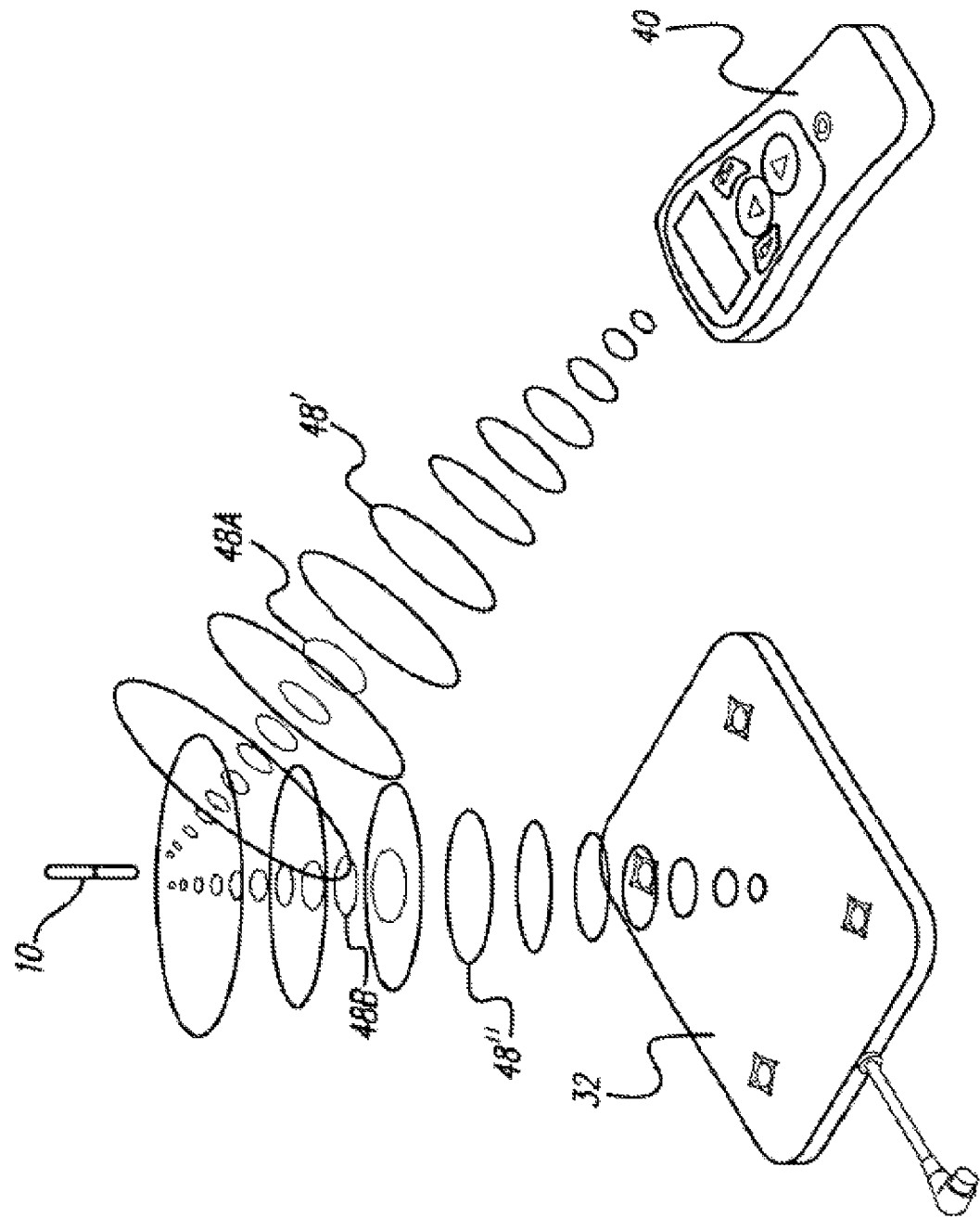
FIG. 22 schematically illustrates a bidirectional telemetry system used with the invention.

Turning next to FIGS. 22-25, a more detailed description of one preferred implementation of an FSK telemetry link is shown. As seen in FIG. 22, a BPB device 10 (a very small device) is implanted in a patient. The implant depth may be several centimeters, so it is important that a telemetry link be capable of functioning over a sufficient distance, e.g., at least 15 cm, and preferably at least 30 cm or more, e.g., 60 cm. The remote control 40 and the chair pad 32 (which is connected to a base station 50 (see FIG. 1) incorporates appropriate antenna coils and transmitting circuitry for sending FSK signal transmissions to the BPB device 10. These FSK signal transmissions sent to the BPB device 10 are symbolically represented in FIG. 22 by the stream of increasingly larger ovals 48' and 48" emanating from the remote control 40 and chair pad 32, respectively. The BPB device 10 includes an FSK receiver circuit, described more fully below, that allows it to receive the FSK transmissions 48' and 48". Similarly, the BPB device 10 includes a transmitter that allows it to send FSK signal transmissions 48A and 48B to the remote control 40 and chair pad 32, respectively.

Not shown in FIG. 22, but present, is a separate OOK-PWM communication link that allows communication signals to be sent from the chair pad 32, i.e., from the base station 50, which is connected to the chair pad (see FIG. 1) to the BPB device 10.

Figure 23:
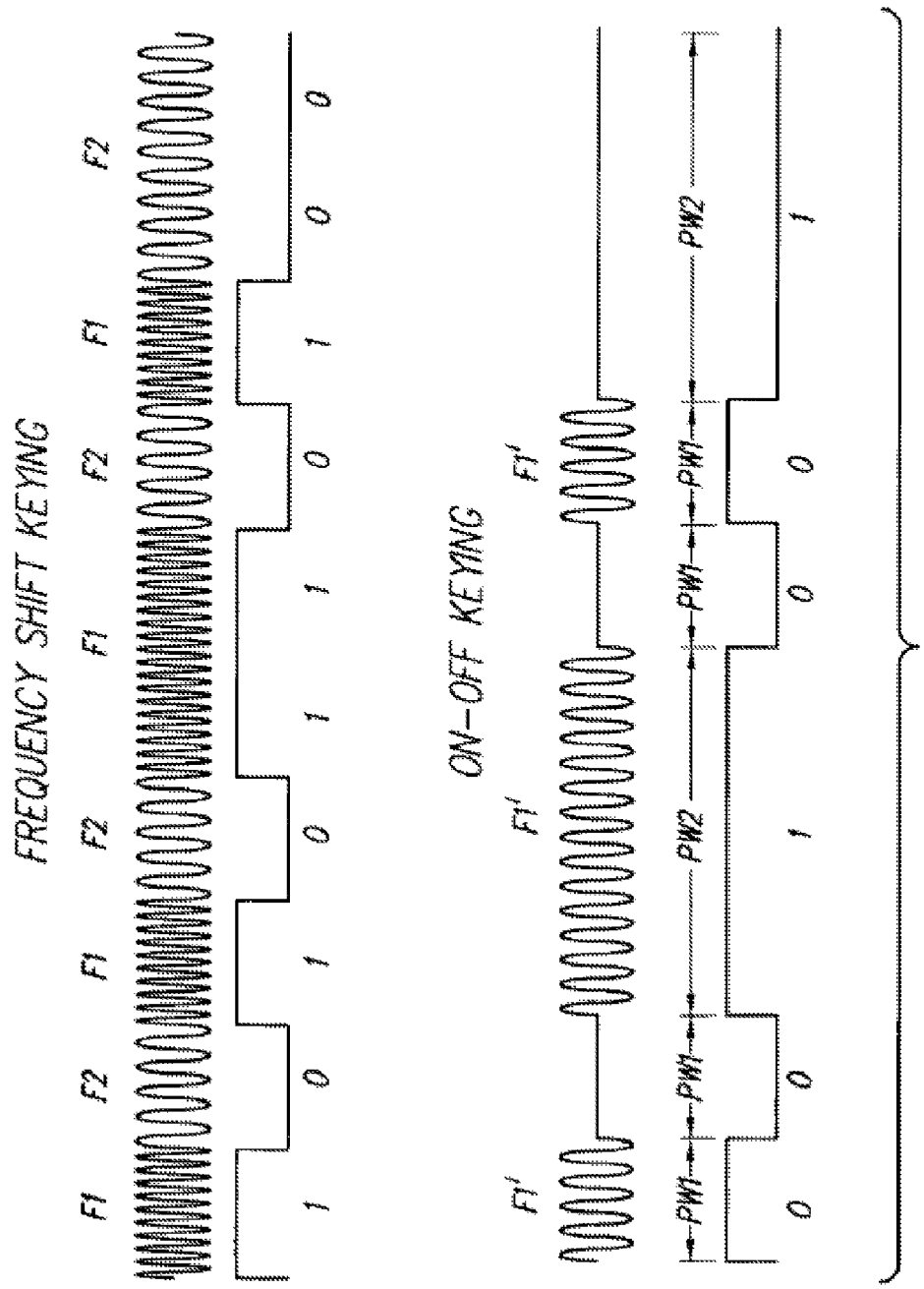
FIG. 23 depicts Frequency-Shift-Keying (FSK) and On-Off-Keying (OOK) modulation techniques used by the bi-directional telemetry system.

FIG. 23 depicts the two types of modulation that are used with the communication links 48 and 38 of the present invention. The primary type of communication used is frequency shift keying, illustrated in the top portion of FIG. 23, wherein the frequency of the transmitted signal varies between two frequencies, F1 and F2. A binary data "1" is represented by the first frequency F1, and a binary "0" is represented by the second frequency F2. The bottom portion of FIG. 23 illustrates an On-Off Keying (OOK)-PWM (pulse width modulation) approach, wherein the transmitted signal comprises either a first frequency F1' or no transmitted signal (frequency equals zero) for one of two pulse widths, PW1 or PW2. A transmitted signal having a first pulse width, PW1, regardless of whether the frequency is F1' or zero (off), is interpreted as, e.g., a binary "0"; whereas a transmitted signal having a second pulse width, PW2, regardless of whether the frequency is F1' or zero (off), is interpreted as, e.g., a binary "1". (Note, this interpretation could just as easily be switched, with a "1" being associated with a PW1 pulse, and a "0" being interpreted as a PW2 pulse.) A change from the F1' frequency to the zero (off) frequency is used to indicate a data transition from one bit to the next bit in the data stream.

Thus, it is seen that in the bottom portion of FIG. 23, and proceeding from left to right, the transmitted signal has a frequency F1' for a width of PW1, indicating a binary "0", followed by a transmitted signal being off (frequency is zero) for a width of PW1, indicating another binary "0"; followed by a transmitted signal of frequency F1' for a pulse width of PW2, indicating a binary "1"; followed by a transmitted signal of frequency zero (signal off) for a width of PW1, indicating a binary "0"; followed by a transmitted signal of frequency F1' for a width PW1, indicating a binary "0"; followed by a transmitted signal of frequency zero (signal off) for a width PW2, indicating a binary "1". Thus, the binary data stream being transmitted in the exemplary signal shown in the bottom of FIG. 23 comprises "001001"

Figure 24:
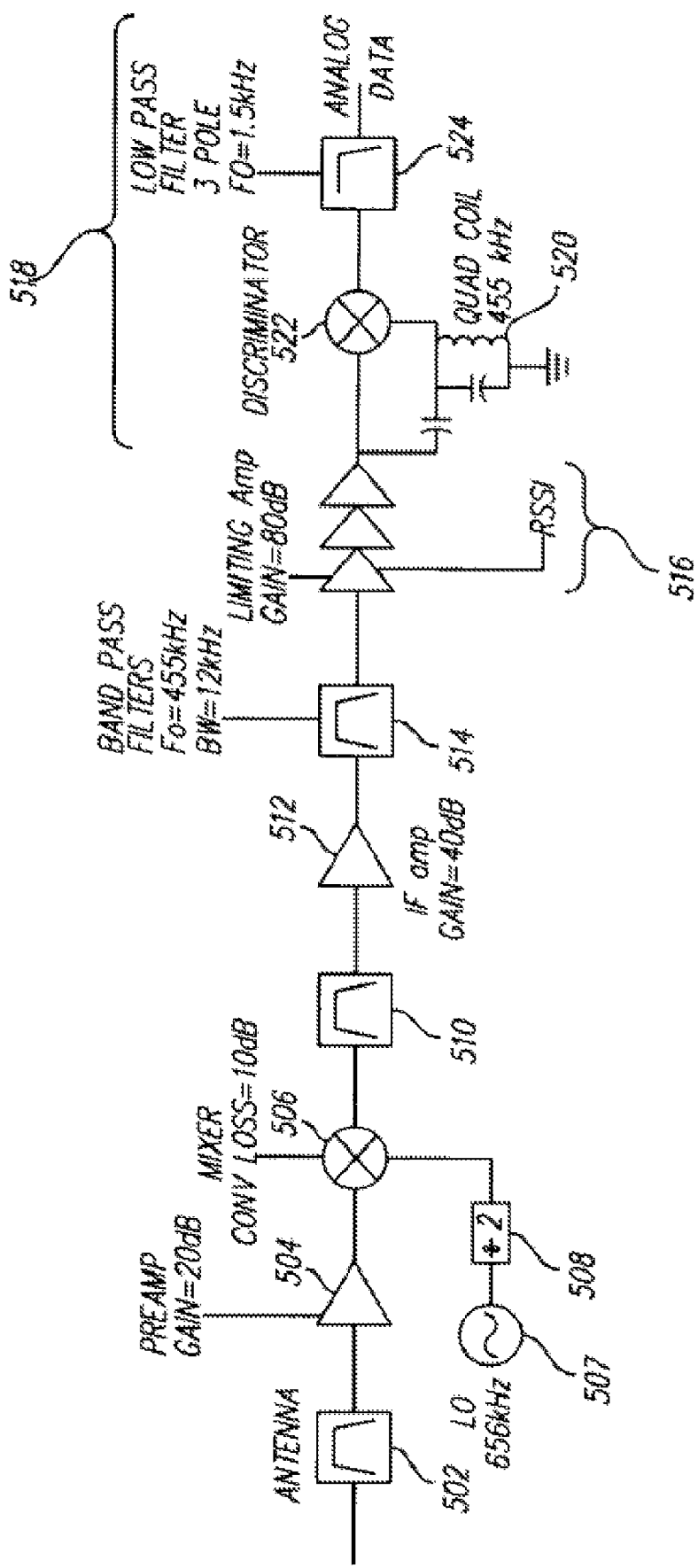
FIG. 24 shows a block diagram of a receiver that may be used in an external device, e.g., a remote control unit, used with the implantable microstimulator.

FIG. 24 illustrates a representative type of FM receiver that may be implemented in the remote control 40, or the base station 50 and chair pad 32, in order to receive the FSK signal transmitted from the BPB device 10. As seen in FIG. 24, such receiver includes an antenna 502 for receiving the FSK signal transmitted from the BSP device 10. This signal is then amplified by a pre-amplifier 504 having a gain of about 20 dB. The amplified signal is then mixed in a mixer 506 with a signal obtained from a local oscillator (LO) 507, reduced by a dividing circuit 508, to produce an intermediate frequency (IF) signal. In one preferred embodiment, the LO frequency is 656 KHz, and is divided by the dividing circuit 508 by two, thereby providing a signal of 323 KHz that is mixed with the incoming FSK signal from the BPB device 10. The loss associated with the conversion to the IF frequency is only about 10 dB.

The IF frequency signal is passed through a bandpass filter 510 and then amplified by amplifier 512, which amplifier has a gain of about 40 dB. The amplified IF signal is then passed through another bandpass filter 514. The center frequency of the bandpass filters 510 and 514 is, in one embodiment, about 455 KHz, and the bandwidth is about 12 KHz. The amplified and filtered IF signal is then subjected to a limiting amplifier 516, having a gain of about 80 dB, and the resulting signal is then passed through a demodulator circuit 518. The demodulator circuit 518 demodulates the FSK data contained in the IF signal to recover the data therein. As depicted in FIG. 24, the demodulator circuit 518 includes a quad coil tuned to 455 KHz, a discriminator (multiplier) circuit 522, and a low pass filter 524. The output from the low pass filter 524 is an analog data stream wherein a "1" is represented by a first amplitude, e.g., +V volts, and a "0" is represented by a second amplitude, e.g., 0 volts.

The remote control receiver circuit depicted in FIG. 24 is a typical FM receiver, not much different from the FM receiver included in a car radio. Advantageously, such receiver is inexpensive to make from readily available parts, is easy to manufacture and test, and uses a reliable and proven architecture.

Next, with reference to FIG. 25, a receiver/transmitter circuit that is used in the BPB device 10, in accordance with one preferred embodiment of the invention, will be described. This circuit provides direct conversion of the incoming FSK signal to data, and as such represents a relatively new approach in wireless technology. Advantageously, the circuit does not require large external components. The circuit uses a BFSK (binary frequency shift key) modulation scheme wherein a "0" is represented by a lower frequency F2, and a "1" is represented by a higher frequency F1. In a preferred embodiment, F1 is 131 KHz, and F2 is 123 KHz. Thus, there is not much frequency difference between F1 and F2. More particularly, the frequency difference is only 8 KHz, which is only about a 6.3% difference between the F1 and F2 frequencies (where the percent difference is calculated as $\{(F1-F2)/[(F1+F2)/2]\} \times 100$). Having F1 and F2 so close to each other in frequency greatly simplifies some of the antenna tuning issues that are present within the BPB device. However, having F1 and F2 so close to each other in frequency also means that great care must be exercised to precisely calibrate the local oscillator so that the BPB electronic circuitry can successfully distinguish between 123 KHz and 131 KHz. Such calibration should occur at body temperature, i.e., about 37° C.

Figure 25:
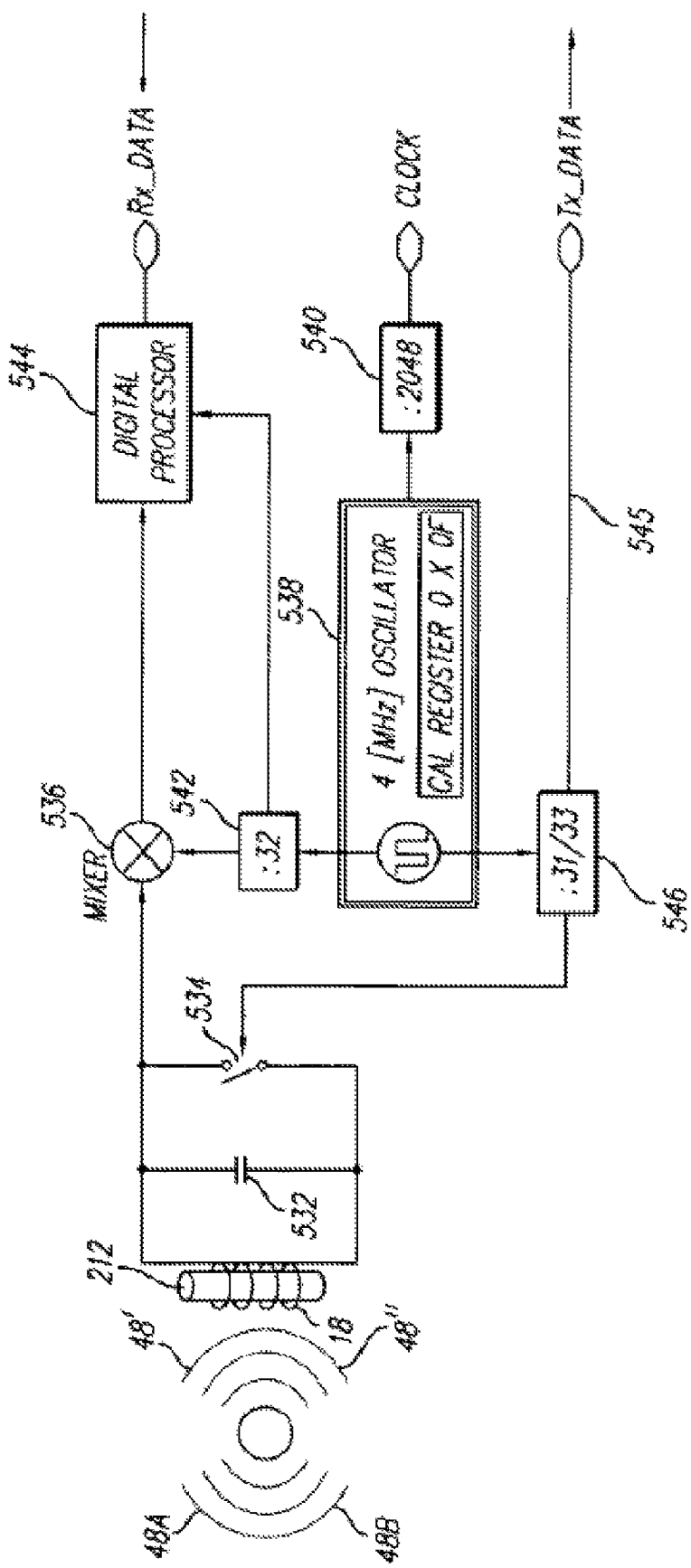
FIG. 25 depicts a block diagram of a representative FSK receiver/transmitter that may be used within the implantable microstimulator.

As seen in FIG. 25, when the circuit operates as a receiver circuit, incoming BFSK signal 48' or 48" is received through an antenna coil that is wrapped around ferrite core 212. A tuning capacitor 532 tunes the coil 18, in combination with the ferrite core 212, so that it optimally receives signals in the 123 KHz to 131 KHz range. A data switch 534 is switched to a first position so that the incoming tuned signal is applied to a mixer circuit 536. A 4 MHz oscillator produces a 4 MHz signal that is divided by 2048 in dividing circuit 540 to produce a 1.985 KHz clock signal. The 4 MHz signal is similarly divided by 32 in dividing circuit 542 to produce a local oscillator signal having a frequency F3 that is also applied to the mixer circuit 536. The local oscillator frequency F3 is 127 KHz, mid-way between the F1 and F2 frequencies. The mixer (or multiplier) circuit 536 multiplies the incoming signal with the 127 KHz local oscillator signal to produce a difference signal, F3±F2 (when the incoming signal is F2), and F3±F1 when the incoming signal is F1). The sum F3+F2 or F3+F1 is filtered out. The signals that remain are F3−F2 and F3−F1. For the indicated frequency values, F3−F2 is 4 KHz, and F3−F1 is −4 KHz (or 0 KHz because negative frequencies don't exist in real time). Thus, it is seen that this difference signal is 4 KHz if the incoming signal is 123 KHz (a binary "0"), and will be 0 KHz if the incoming signal is a binary "1". The resulting signal (4 KHz or 0 KHz) is applied directly to the digital processor 544 used within the electronic subassembly 14 of the BPB device 10.

The processor 544 is able to readily ascertain whether such signal is a 4 KHz signal or a 0 KHz signal, and is therefore able to readily assign a "1" or "0" value to the data bit signal. One technique that may be used to readily distinguish a 4 KHz signal from a 0 KHz signal within a digital processor is to apply the signal as a clock signal to a register that is hardwired to fill with "1's" as it is clocked. After a prescribed period of time (e.g., a data clock time, or the duration of a data bit, or a portion of a data bit) the contents of the register are checked, and if a high value, then a determination is made that the incoming data bit must be a "1", and if a low value, then a determination is made that the incoming data bit must be a "0".

When used as a transmitter, the data switch 534 is switched to a second position that allows data to be transmitted from the antenna coil 18 as data 48A or 48B. Data to be transmitted is received on Tx Data line 545 and is converted to either a 123 KHz signal (to represent a binary "0"), or to a 131 KHz signal (to represent a binary "1"). Such conversion to BFSK data is done with the help of the 4 MHz oscillator signal and a divide-by-31 or -33 circuit 546.

The OOK-PWM receiving circuit used within the BPB device may use the same antenna coil 18 as does the BFSK circuit. In fact, the coil 18, and many of its related components, serves multiple functions using the principles described, e.g., in U.S. patent application Ser. No. 09/799,467, filed Mar. 5, 2001; and Ser. No. 10/133,766, filed Apr. 26, 2002, both of which applications are assigned to the same assignee as is the present application, and both of which applications are incorporated herein by reference. The OOK-PWM transmitter circuit used within the base station 50 and charging pad 32 may be of conventional design.

As described above, it is thus seen that the receiver and transmitter circuit used within the BPB device 10, and shown in FIG. 25, offers the following features and advantages: (1) it is able to receive and send data across body/air reliably; (2) it is simple, having only a few components; (3) it works well after initial calibration; (4) it requires only one external coil and capacitor, may be fabricated in a small space, and consumes very little power; (5) it has an approximate range of 60 cm; (6) it has a response time of less than 2 seconds; (7) it experiences a minimum number of errors, e.g., on the order of 1 command error per year for every 10,000 users; and (8) for safety and other technical reasons, a backup or second telemetry system is included for getting data into the BPB device.

Figure 4:
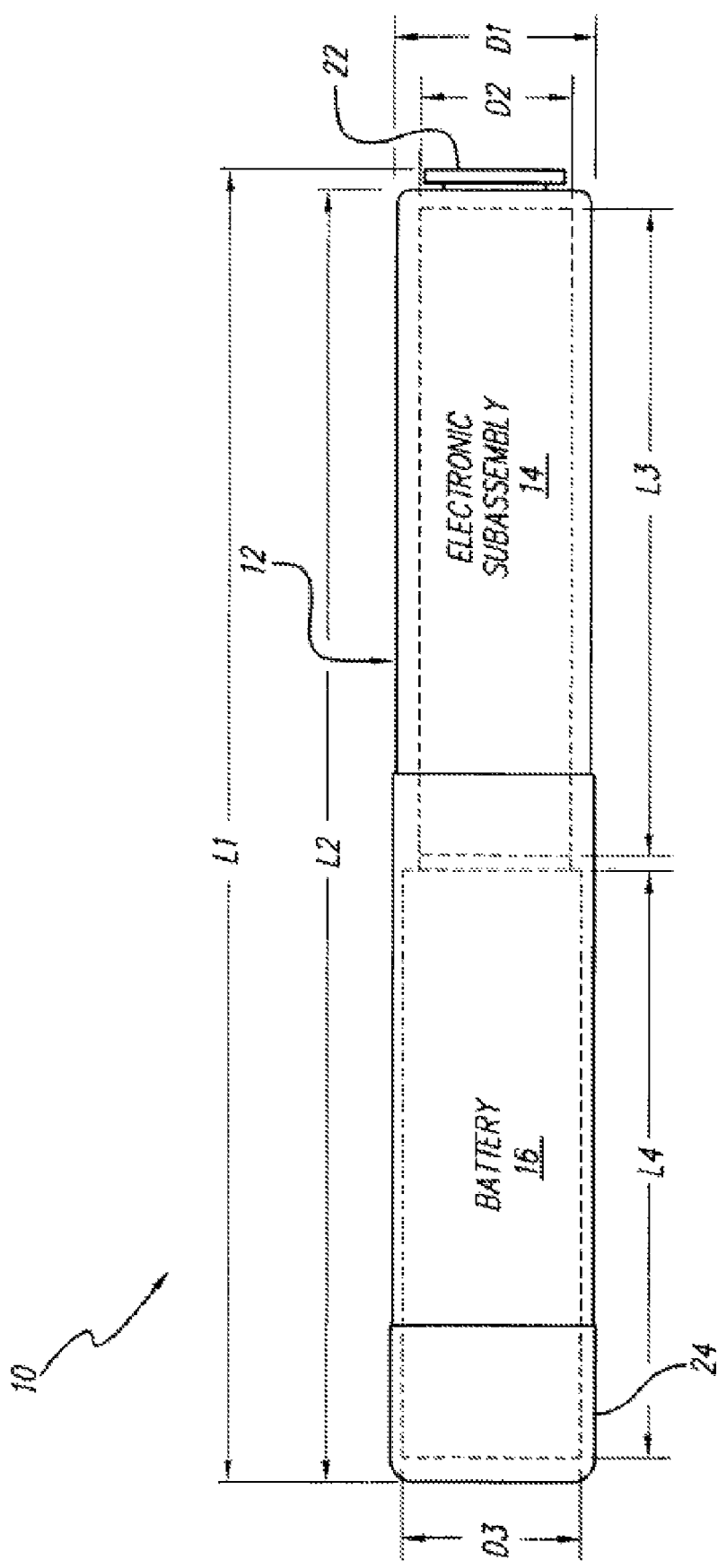
FIG. 4 is an enlarged side view showing the overall descriptive dimensions for the battery-powered BION case, the battery, and the electronic subassembly.

Referring now to FIG. 4, a side view of the BPB case 12 is shown depicting exemplary overall dimensions for the case 12 and BPB internal components. The BPB case 12 functions together with the additional components of BPB device 10, including the BPB battery 16 and the BPB electronic subassembly 14, to provide the stimulating function of the device. As shown in the figures, BPB case 12 may have a tubular or cylindrical shape with an outer diameter shown in FIG. 4 as D1 having a minimum value of about 3.20 mm and a maximum value of 3.7 mm, and preferably a maximum value of about 3.30 mm. The inner diameter of the portion of the BPB case 12 enclosing the electronic subassembly 14 is shown in FIG. 4 as D2 with a minimum value of about 2.40 mm and a maximum value of about 2.54 mm. The inner diameter of the portion of the BPB case 12 enclosing the BPB battery 16 is shown in FIG. 4 as D3 with a minimum value of about 2.92 mm and a maximum value of about 3.05 mm. The length of the BPB case 12 is shown in FIG. 4 as L1 with and is no greater than about 30 mm, and preferably no greater than about 27 mm (L1 includes the length of the case housing plus the stimulating electrode 22). The length L2 of the case 12 has a value of about 24.5 mm. The portion of the case 12 enclosing the electronic subassembly 14 is shown in FIG. 4 as length L3 with a maximum value of about 13.00 mm. The portion of the case 12 enclosing the BPB battery (or other power source) 16 is shown in FIG. 4 as length L4 with a value of about 11.84 mm. These dimensions are only exemplary, and may change, as needed or desired to accommodate different types of batteries or power sources. For example, the BPB device, instead of being cylindrically shaped, may have a rectangular or oval cross section having a width and height that is no greater than about 3.3 mm, and an overall length is no greater than about 27 mm. To help protect the electrical components inside the BPB device 10, the case 12 of the BPB device 10 is hermetically sealed. For additional protection against, e.g., impact, the case 12 may be made of metal (e.g., titanium), which material is advantageously biocompatible. The BPB case 12 is preferably, but not necessarily, Magnetic Resonance Imaging (MRI) compatible. The manufacturing/assembly process of the BPB device 10 will be discussed in detail below.

The BPB device 10 includes a battery 16. The battery 16 may be a primary battery, a rechargeable battery, or other power source, as previously described. When the battery 16 is rechargeable, it is recharged, as required, from an external battery charging system 39 typically through the OOK-PWM telemetry link 38 (as shown in FIG. 1).

The BPB device 10 includes a processor and other electronic circuitry that allow it to generate stimulating pulses that are applied to a patient through electrodes 22 and 24 in accordance with a program stored in programmable memory located within the electronic subassembly 14. The processor and other electronic circuitry also provide the telemetry functions described herein.

Figure 5:
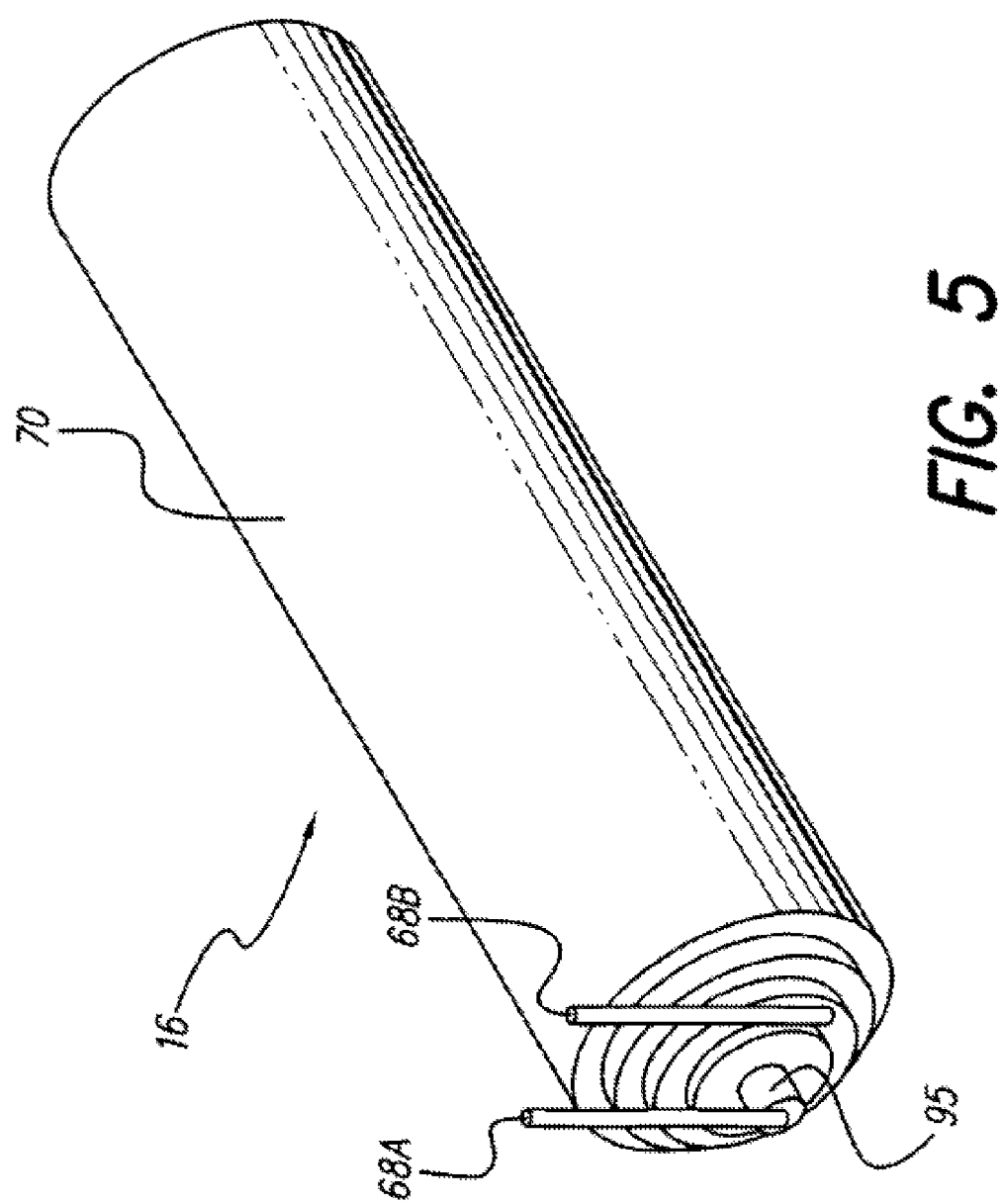
FIG. 5 is a perspective view of the battery and connecting wires.

The battery 16 shown in FIG. 5 is a self-contained battery which powers the BPB device 10. The battery 16 may be a Lithium-ion battery or other suitable type of battery or power source. One type of rechargeable battery that may be used is disclosed in International Publication WO 01/82398 A1, published 01 Nov. 2001, and/or WO 03/005465 A1, published 16 Jan. 2003, which publications are incorporated herein by reference. Other battery construction techniques that may be used to make the battery 16 used with the BPB device are as taught, e.g., in U.S. Pat. Nos. 6,280,873; 6,458,171 and U.S. Publications 2001/0046625 A1 and U.S. 2001/0053476 A1, which patents and publications are also incorporated herein by reference. Recharging (when needed) occurs from an external charger to an implant depth, e.g., up to 13.87 cm. At this distance, charging from 10% to 90% capacity can occur in no more than eight hours. The battery 16 functions together with the additional components of the BPB device 10, including the BPB case 12 and the BPB electronic subassembly 14 to provide electrical stimulation through the electrodes 22 and 24. The battery or power source 16 has a pin 95 protruding from the flat end for the positive polarity contact. This pin has a protruding length, e.g., of 0.25 mm and is embedded internally throughout the length of the cathode case of the battery 16. The pin 95 may be made of platinum or other suitable anode material. Wires 68A and 68B are used for connecting the battery 16 to the electronic subassembly 14. Wire 68A is insulated and laser welded or otherwise electrically connected to the pin 95, and wire 68B is not insulated and is laser welded or otherwise electrically connected to the case of the battery. The battery case 70 has a negative polarity. The battery's nominal voltage is typically 3.6 V, measured during a first cycle C/5 discharge. The battery's nominal capacity, C, is no less than 2.5 mAh (milli-amp-hours) when measured after the third discharge cycle with C/2 charge to 4.0V and C/5 discharge to 3.0V at 37° C. (C/2 charge means that it takes 2 hours for the battery 16 to charge. C/5 discharge means that it takes 5 hours for the battery 16 to discharge.) Charge or discharge time is calculated by taking the capacity (mAh or Ah) and dividing it by current (mA or A). The nominal settings are 4 mA amplitude, 20 Hz pulse frequency, 200 μsec pulse width, 5 sec burst-on, 5 sec burst-off, and 200 μA recovery into a 1000Ω resistive load.

The electronic subassembly 14, shown in FIG. 1, functions together with the additional components of the BPB device 10, including the BPB case 12, BPB battery 16, and electrodes 22 and 24, to provide the BPB device stimulating function. In one preferred embodiment, the electronic subassembly 14 fits within, for instance, a cylinder with an outer diameter D2 and length L3 as shown in FIG. 4. The inner diameter D2, has a minimum value of about 2.40 mm and a maximum value of about 2.54 mm. The length L3, has a maximum value of about 13.00 mm.

The electronic subassembly 14 contains circuitry for stimulation, battery charging (when needed), telemetry, production testing, and behavioral control. The stimulation circuitry can be further divided into components for high voltage generation, stimulation phase current control, recovery phase current control, charge balance control, and over voltage protection circuitry. The telemetry circuitry can be further divided into an OOK receiver, FSK receiver, and FSK transmitter. The behavioral control circuitry can be further divided into components for stimulation timing, high voltage generation closed loop control, telemetry packet handling, and battery management. In addition to these functions, there is circuitry for reference voltage and reference current generation, system clock generation, and Power-On Reset (POR) generation. The coil 18 (shown in FIG. 1) is utilized for receiving power for battery charging (when used), telemetry, and high voltage generation.

The charging circuitry within the electronic subassembly 14 detects the presence of an external charging field within no more than 5 seconds of the application of such a field. Upon detection, the BPB device 10 enables a mode in which it can receive a telemetry message and in which it can recharge the battery 16, as necessary. The electronic subassembly 14 measures the rectified voltage during recharging and is able to transmit the measured voltage value to the base station 50 via coil 34. The battery voltage measurements are made in relatively identical conditions. Specifically, the battery voltage is measured when no stimulation pulse is being delivered.

When the BPB device utilizes a rechargeable battery, and when the voltage is less than the voltage defined by the Battery Recharge Upper Voltage Limit Internal Register (BRUVLIR), the BPB device 10 charges the battery 16 using constant current charging with a maximum current of C/2. The constant current phase of charging ends and the constant voltage phase of charging begins when the BPB voltage reaches the voltage defined by the BRUVLIR.

During the constant voltage phase of charging, the charging circuitry maintains the battery 16 charging voltage at the voltage defined by the BRUVLIR. When the constant voltage charging current falls to 400 μA or less (i.e., when full charge has been reached), the charge ready bit of the BPB status register is activated and charging may be completed by the removal of the magnetic field. During charging, the BPB charging circuitry monitors the incoming magnetic energy and periodically sends information to the base station 50 via coil 34 in order to minimize the magnetic field that the BPB device 10 is exposed to, thus minimizing the electrical dissipation of the BPB device 10 while charging. U.S. Pat. No. 6,553,263, incorporated herein by reference, describes relevant charging technology which may also be used.

Protection circuitry within the electronic subassembly 14 is used as a failsafe against battery over-voltage. A battery protection circuit continuously monitors the battery's voltage and electrically disconnects the battery if its voltage exceeds 4.1 V. The BPB device 10 is not able to recover from an excessive voltage condition, and thus requires explantation should an over-voltage condition occur, where an over-voltage condition is defined as a voltage that exceeds 4.1 V.

Figure 6:
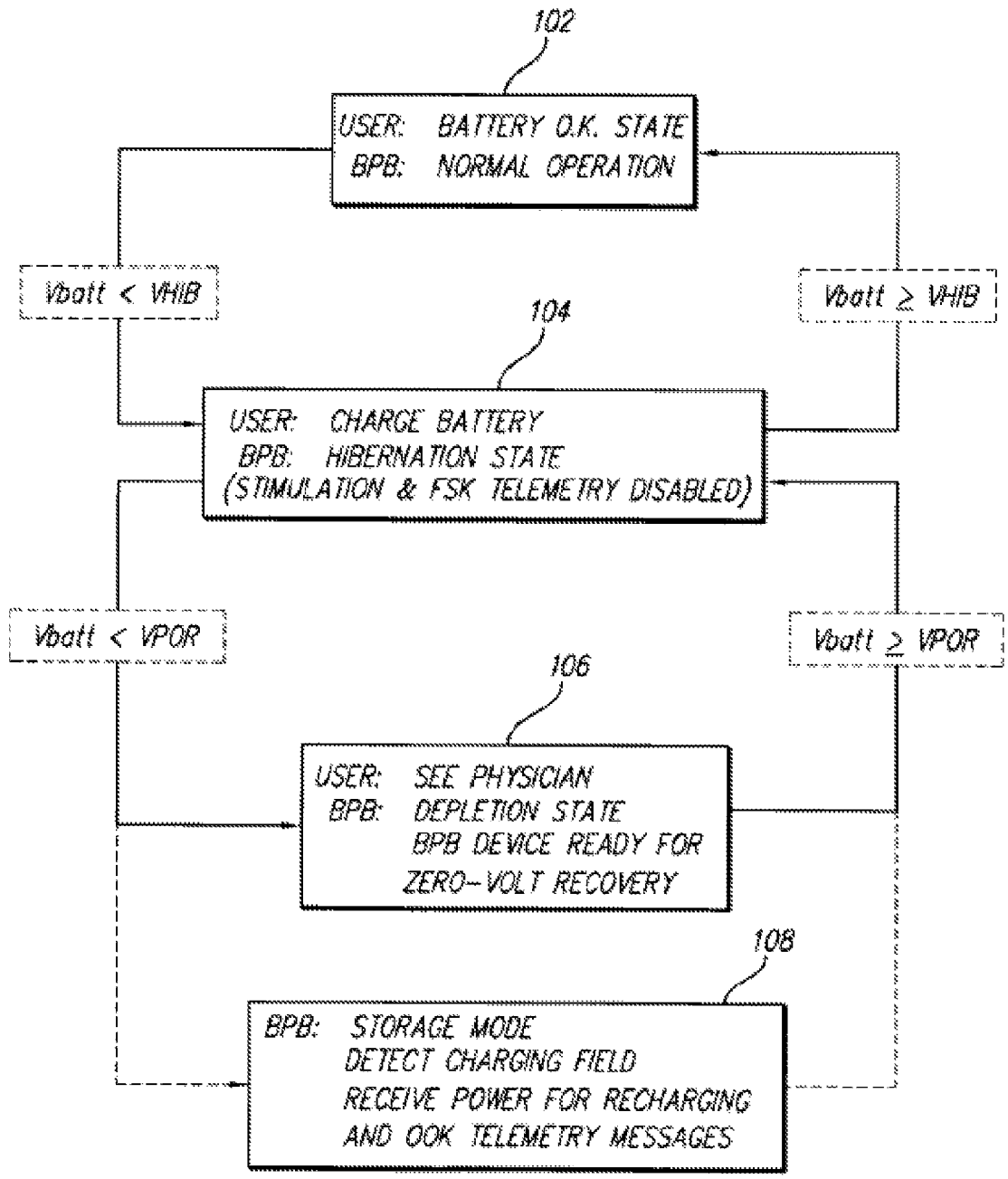
FIG. 6 is a block diagram representing the battery states based on measured battery voltage.

The BPB device 10 has different states based on the measured battery voltage, Vbatt. (Vbatt is measured when no stimulation is being delivered). FIG. 6 represents these various states and transitions between states. The BPB device 10 should normally be in Normal Operation State 102, but when the measured battery voltage, Vbatt, falls below the voltage defined by the battery voltage hibernation level internal register, VHIB, the device enters a low-power Hibernation State 104. VHIB is a programmable voltage value of hibernation threshold for the battery 16. In the Hibernation State, stimulation and FSK telemetry are discontinued. In other words, the BPB device 10 discontinues listening for an incoming FSK telemetry signal but continues to listen for an incoming OOK telemetry signal. In the Hibernation State 104, the BPB device 10 is able to detect an applied external charging field. The Hibernation State 104 persists until the battery voltage, Vbatt, exceeds the programmable value of VHIB, where VHIB is programmable between 3.25 V and 3.6 V. The battery 16 then goes back to Normal Operation State 102 and the stimulation and FSK telemetry signals resume when Vbatt becomes greater than the programmed value±0.05 V.

While in the Hibernation State 104, the battery 16 may also enter the Depletion State 106 when Vbatt falls below a non-programmable voltage value of Power On Reset (VPOR) threshold for the battery 16 of between 2.2 V and 2.8V. In the Depletion State 106, the stimulation and FSK telemetry are discontinued and are only able to be resumed following programming and recharging by a clinician. The BPB device 10 disables all circuitry except what is required for recharging the battery when an RF charging field is applied. While in the Depletion State 106, the BPB circuitry is able to recharge the battery 16 from an external charging field. Charging while in the Depletion State 106 is performed at a slow rate (trickle charge) to allow the battery to recover from a low voltage condition. The BPB device 10 performs a power-on reset when Vbatt exceeds VPOR, then the BPB device 10 returns back to the Hibernation State 104.

The BPB device 10 can also be set in Storage Mode 108. In Storage Mode 108, the BPB device 10 shuts down the circuitry in order to conserve power and the stimulation and FSK telemetry is disabled. In Storage Mode 108, the BPB device 10 is able to detect a charging field and is able to receive both power for recharging as well as OOK telemetry messages via a charging field.

The BPB device 10 contains an inductive coil 18 utilized for receiving power and telemetry messages through an inductive telemetry link 38. The coil 18 may also be utilized to implement additional functions, including voltage conversion. The BPB coil 18 contained in the electronic subassembly 14 has an exemplary cylindrical shape and is constructed from multiple turns of conductive wire around a two-piece exemplary dumbbell shaped ferrite core. Assembly of the BPB coil 18, internal electronic components, and the two-piece ferrite core will be discussed in more detail presently.

Turning back to FIG. 1, the remote control 40 provides clinician programming of the BPB device 10 and limited stimulation control for the patient following implantation via a bidirectional FSK telemetry link 48. (As stated earlier, an IrDA direct link 44 is provided to interface between the clinician's programmer 60 and the remote control 40.) The remote control 40 is small and light enough to be held comfortably in one hand and fits inside a purse or pocket. Its smallest dimension is no more than 3 cm and its largest dimension is no more than 11.5 cm. The remote control 40 operates on standard (e.g., off-the-shelf) batteries, such as AAA batteries.

Figure 7:
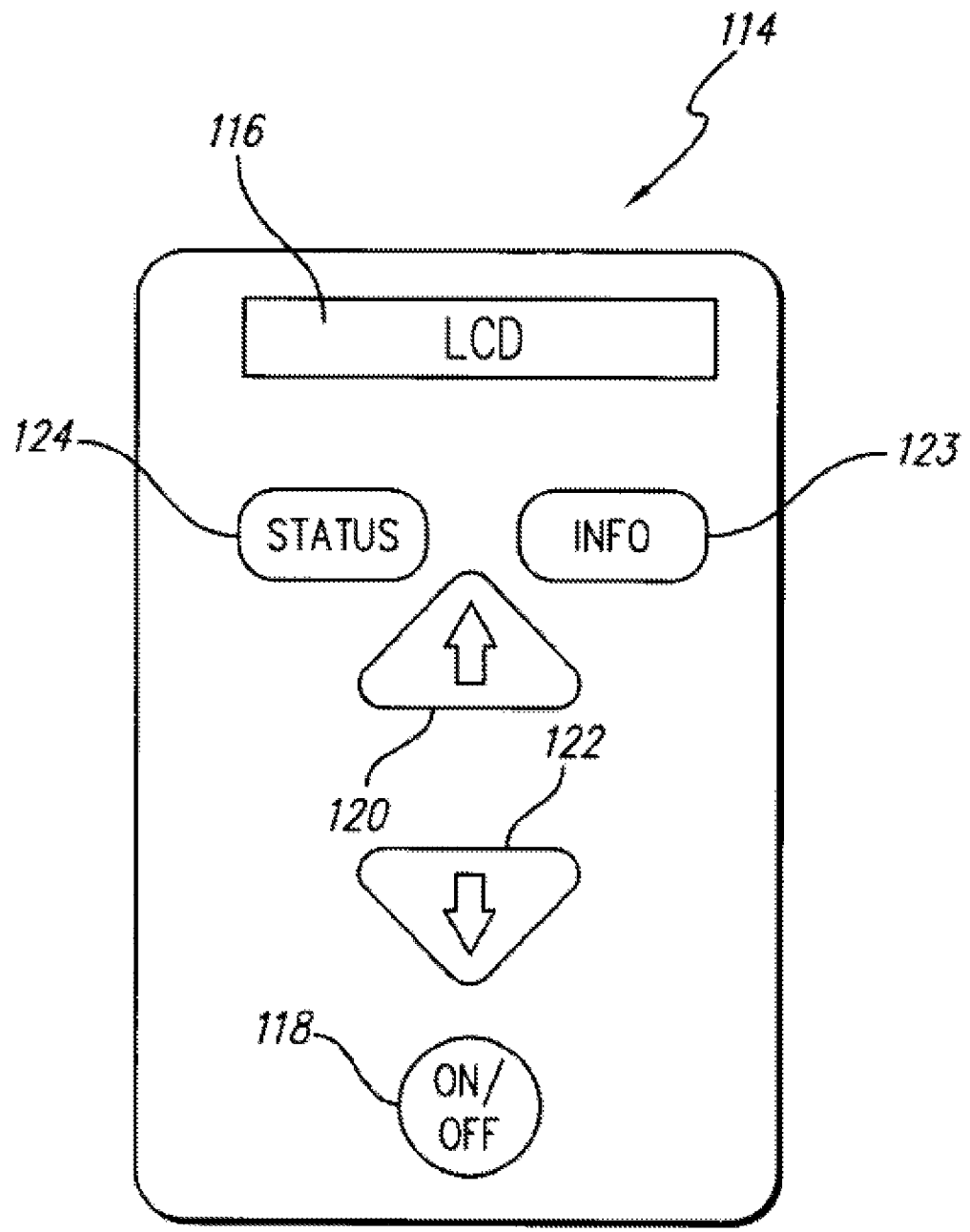
FIG. 7 is a front view of a representative remote control panel showing exemplary front panel components.

An exemplary front panel 114 of the remote control 40 is shown in FIG. 7, which identifies the primary control keys. An LCD display 116 shows all values and messages, e.g., whether stimulation is enabled or disabled or the battery's energy level or state (normal, hibernation, depletion, or storage). The following control keys are found in the front panel 114: ON/OFF key 118, up arrow key 120, down arrow key 122, information key 123, and status key 124. All control keys are easily manipulated and may be recessed so that they are not accidentally activated (e.g., when the remote control 40 is in a purse).

The Clinician's Programmer (CP) 60 controls an implanted BPB device 10 by communicating with an External Controller (the Remote Control 40 or charging system 39). External Controller 39 or 40 in turn conveys commands to the BPB device 10 through an FSK telemetry link 48. A clinician has three ways to start up the CP program—"New Patient", "Find Patient" and "Scan for BION". The "New Patient" option brings up a blank form for the clinician to fill in the patient demographic information such as name, birth date, identifying number, address, contact information, and notes. The "Find Patient" option brings up a menu of previously entered patient records for selection. Upon selection of a patient, the saved patient information is displayed for review. The "Scan for BION" option determines whether or not there is a BPB device 10 within telemetry range. If so, the identification number (ID) of the BPB device 10 is obtained and the database is searched for a patient whose implanted BPB device 10 ID matches the one found. If such a match is found, the patient's demographic information is automatically displayed for review.

Once a patient for the BPB device has been identified, the clinician can then adjust stimulation parameters through the Parameter Test utility. The successful stimulation parameter sets can be saved to the patient's record in the database. Previously saved parameter sets can be reviewed and re-applied using utilities to view history or current settings. The current battery level of the BPB device 10, as well as records of the recharge times, can be viewed.

The Clinician's Programmer 60 may also be used to generate different types of reports, such as Patient Information, Session Summary, Implant System, and Visit History. The Patient Information report includes all of the patient's demographic information. The Session Summary report summarizes the events for the follow-up session. The Implant System report details the information for the implanted BPB device 10 and any external controllers assigned to the patient. The Visit History shows information about office visits for the patient in the desired date range. The Clinician's Programmer 60 includes utilities to backup and restore the database. A utility is also available for exporting selected patient information into a data format for transfer.

As described earlier, the charging system 39 shown in FIG. 1, which includes the base station 50 and the chair pad 32, is used to transcutaneously charge the BPB battery 16 (when needed), and it is also used to communicate with and control the BPB device 10 via an OOK telemetry link 38 and/or an FSK bidirectional telemetry link 48. Most of the electronics of charging system 39 are housed in a stand-alone package, with the exception of an AC adapter 54 for connection with a wall AC power socket 52. The charging system 39 also provides feedback to the user regarding the status of the BPB battery 16 during recharging. The remote control 40 and the clinician's programmer 60 may be linked via an IrDA interface 45 to the charging system 39 to facilitate exchange of data.

Figure 8:
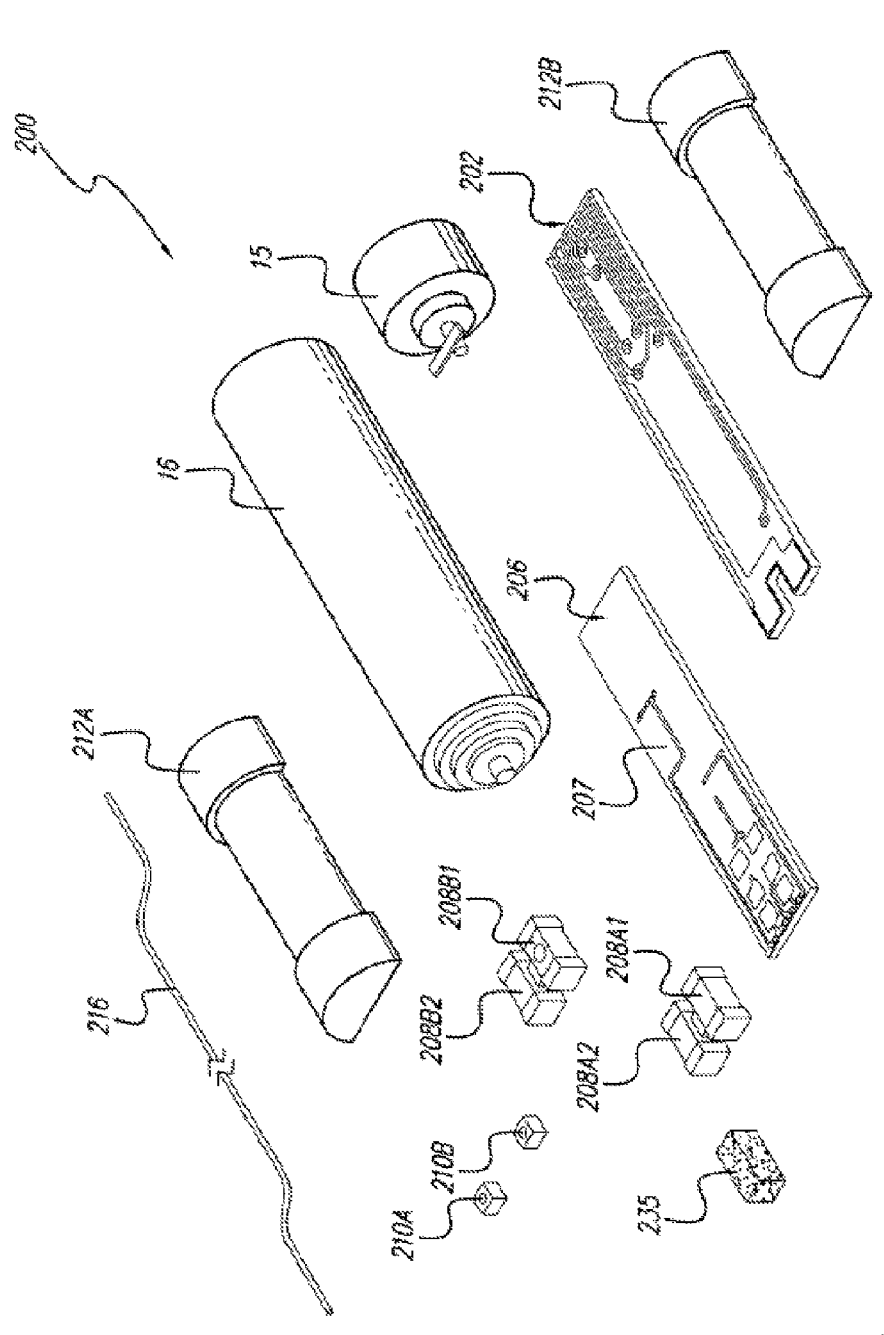
FIG. 8 is an exploded view of the internal components of the BPB device.

An exemplary manufacturing/assembly process of the BPB device 10 will next be described. Unassembled BPB internal components 200 are shown in FIG. 8 and their interactions once assembled are depicted in the functional block diagram of FIG. 21. The components 200 include panel 202; integrated circuitry 206; capacitors 208A1, 208A2, 208B1, and 208B2; diodes 210A and 210B; two ferrite halves 212A and 212B; battery 16; stimulating capacitor 15; molecular sieve moisture getter material 235; and unwound conductive coil wire 216. After the final assembly process, the components 200 are encapsulated within, for instance, a hermetically-sealed housing which consists of two cylindrical shell housings, e.g., a titanium housing 213 and a ceramic housing 215 (both shown in FIG. 20B). Other suitable housing material(s) and shapes may be used.

The BPB assembly process consists of a series of assembly operations that, herein, are grouped into three stages. The first stage comprises operations for putting together sub-assembly 200A (shown in FIG. 14A) and further operations to create sub-assembly 200B (shown in FIG. 15A) from sub-assembly 200A and other components; the second stage comprises creating sub-assembly 200C (shown in FIG. 19) from sub-assembly 200B and other components; and the third stage comprises a process in which the sub-assembly 200C is encapsulated within the exemplary hermetically-sealed cylindrical housing (shown in FIG. 20A). Materials used for the manufacturing/assembly process are only exemplary and other suitable materials may be used.

Figure 9:
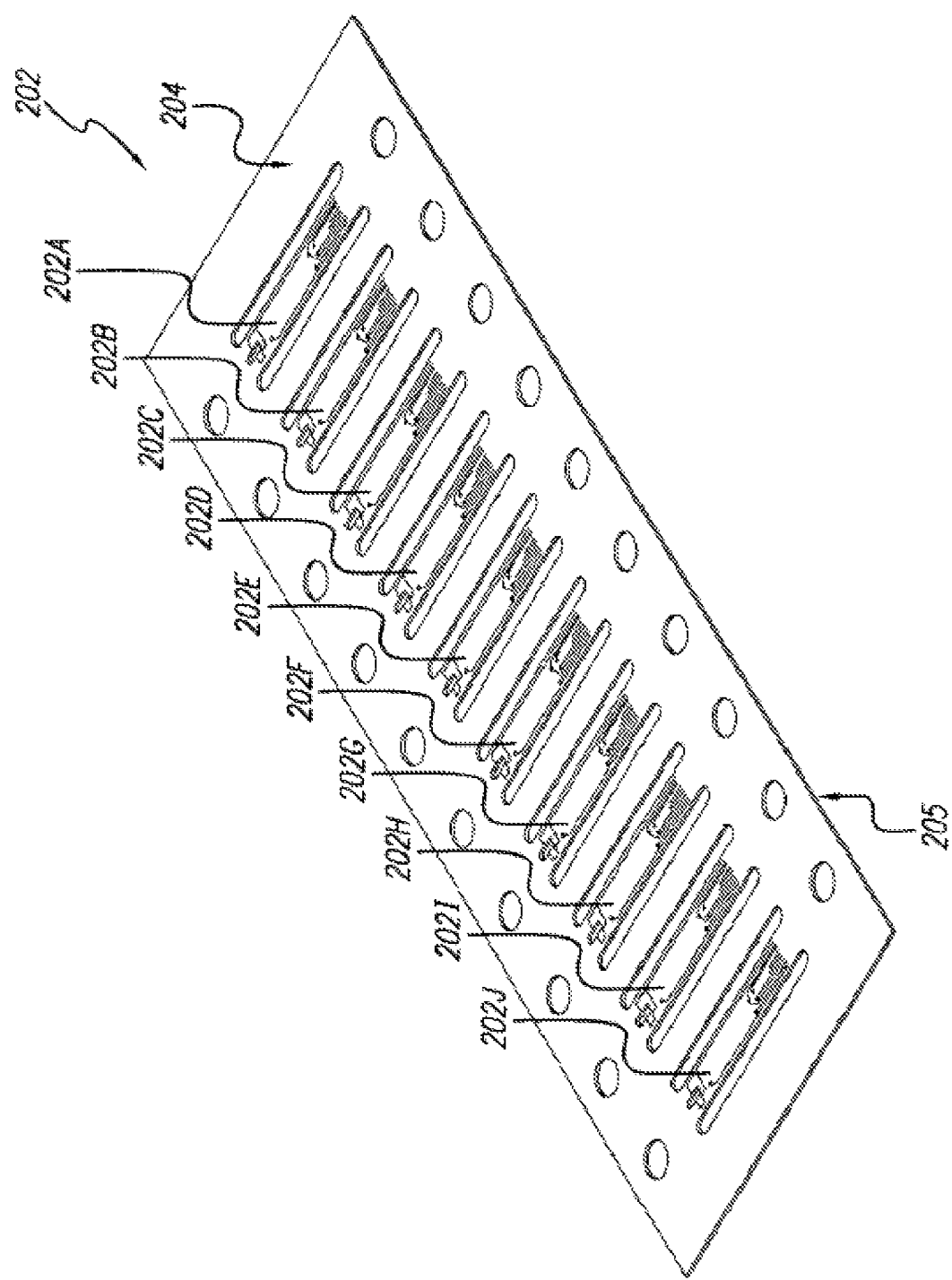
FIG. 9 is a perspective top view of the internal electronic panel in a batch configuration.

With reference to FIGS. 8-16 and 21, the first assembly stage will be described. Ten or more units may be assembled together for batch processing as illustrated in FIG. 9 in which the substrate panels (202A, 202B, 202C, . . . herein also collectively referred to as 202n) are shown as part of panel assembly 202. By using a batch process, starting with the substrate panel assembly 202, the assembly procedure and testing is more efficient as opposed to assembling each unit individually. The substrate panel assembly 202 is a single layer, double-sided circuit board made of ceramic, organic, or other suitable flexible material(s). The contour of each panel 202n of the substrate panel assembly 202 may be precut and only small portions of the edges may be left attached to the substrate panel assembly 202. The small portions that are left intact make the alignment of other components and future singularization of each panel 202n much easier, especially when all other parts have been assembled to the substrate panel assembly 202.

As an initial assembly step, the top surface 204 of substrate panel assembly 202 is used to mount other components, such as the integrated circuit 206, which is similar in shape to each of the substrate panels 202n. The top surface 204 of the substrate panel assembly 202 is identified by a printed part number made during the manufacturing of the substrate panel assembly 202. Each panel 202n of substrate panel assembly 202 is uniquely serialized using a laser beam. The serial numbers are engraved on the bottom surface 205 of the substrate panel assembly 202, and metal pads 203A and 203B (shown in FIGS. 14C, 14D, and 15C) carry the serial number, which metal pads are used for test probing during several steps of the assembly process. Two ferrite half cylinders 212A and 212B "sandwich" a separated panel 202n and associated integrated circuit 206. This "sandwich" design maximizes the size of the half cylinders 212A and 212B and the coil 18 which receive the power transfer from the external coil, thus, maximizing the magnetic inductance.

Figure 13:
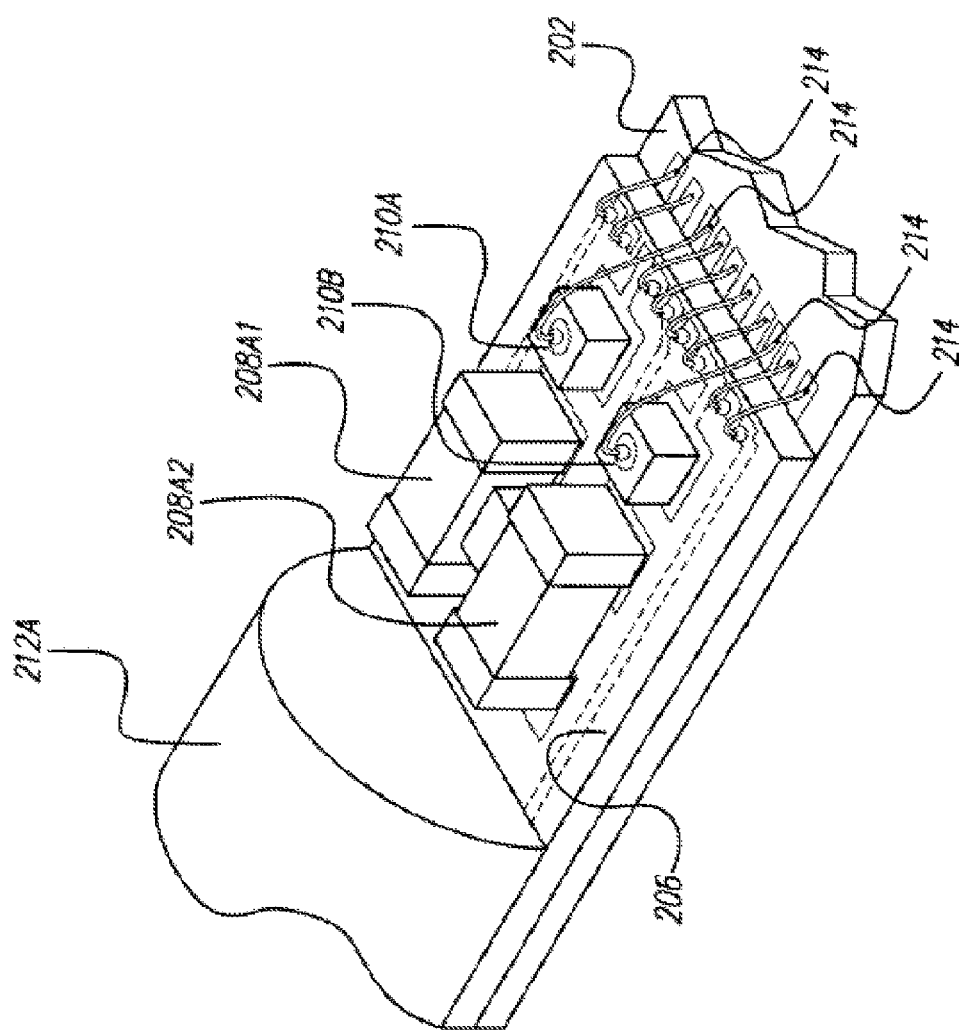
FIG. 13 is an enlarged detail view of the assembled components shown in FIG. 12 depicting the connecting electrical wires.

The integrated circuit (IC) 206 is a custom designed IC chip. The IC wafer, which includes a multitude of these custom ICs 206, is made using standard IC manufacturing processes. The IC wafer is then taken through a post-process called redistribution: A layer of polyamide (or other suitable insulation) is deposited on the IC surface. Photosensitive material is deposited and exposed, e.g., through a mask, in only selected areas, as in photochemical etching processes known in the art. The photosensitive material and portions of the polyamide are removed, for instance, to expose the aluminum pads on the surface of the IC. A layer of titanium tungsten in applied in a similar manner (i.e., using photosensitive etching or the like) to the aluminum. A layer of copper is then deposited, and photochemical etching or the like used to remove the areas of copper that are not needed. This layer of copper (aided by the surrounding layers) creates the "redistribution" of mounting pads and traces that allows secondary components such as diodes 210A and 210B and capacitors 208A1 and 208A2 to be assembled above and bonded to the IC 206 and allows simplified interconnections between the IC 206 and the substrate 202n, as shown in FIG. 13. Again using photochemical etching or the like, titanium tungsten or other suitable bonding material is applied to select portions of the copper, where gold or other suitable conductive material will be applied. Another layer of polyamide or similar insulation is applied (via photochemical etching or the like) to select areas. A layer of gold or other conductive material is applied (again, via photochemical etching or the like) to the bonding material that was earlier applied to the copper. These added layers on the IC surface 207 also provide a damping media for protection against the stresses and damages caused by assembly handling and component placement.

Figure 10:
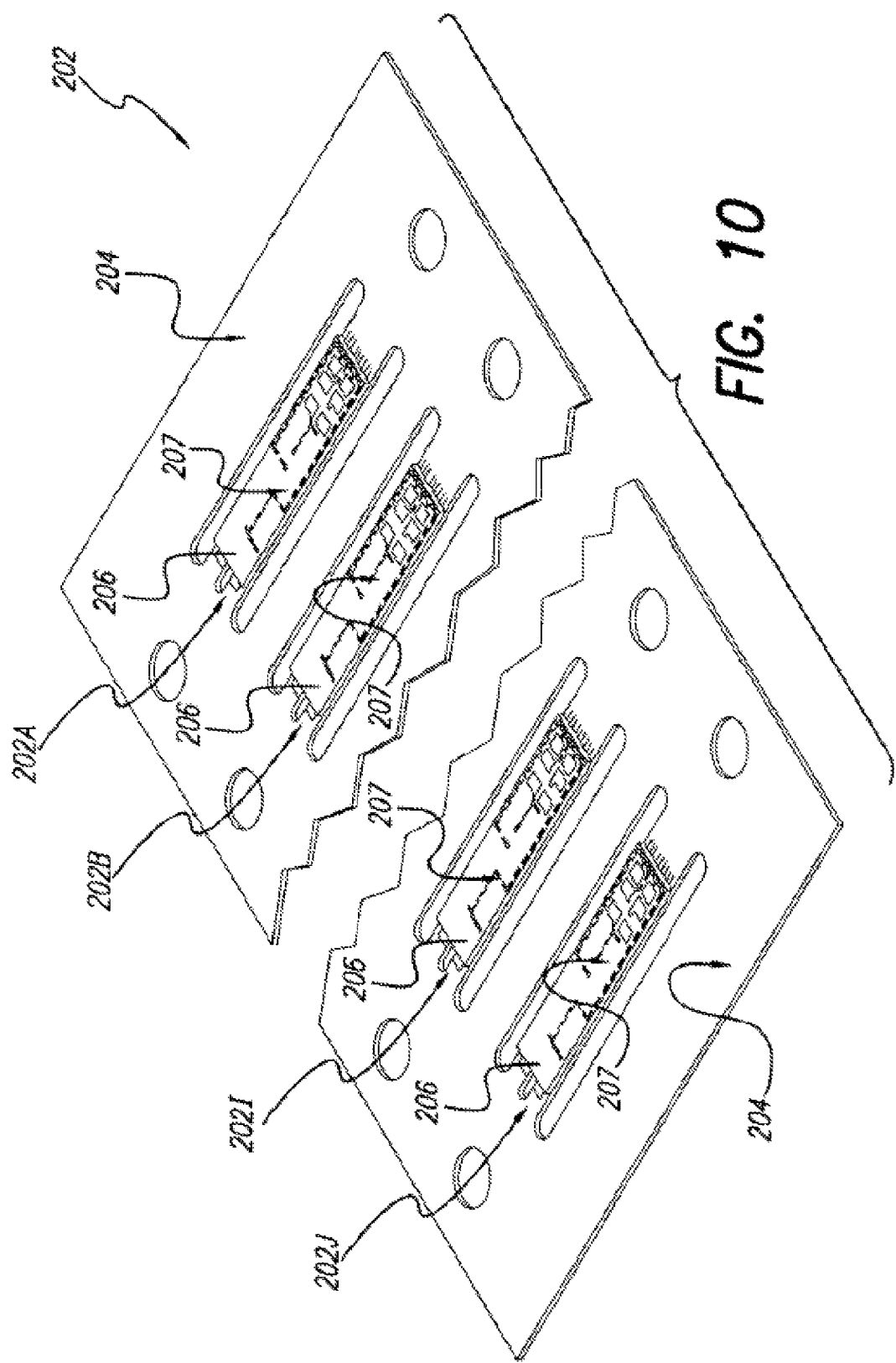
FIG. 10 is a perspective top view of the panel shown in FIG. 9 with the integrated circuitry attached.
Figure 11:
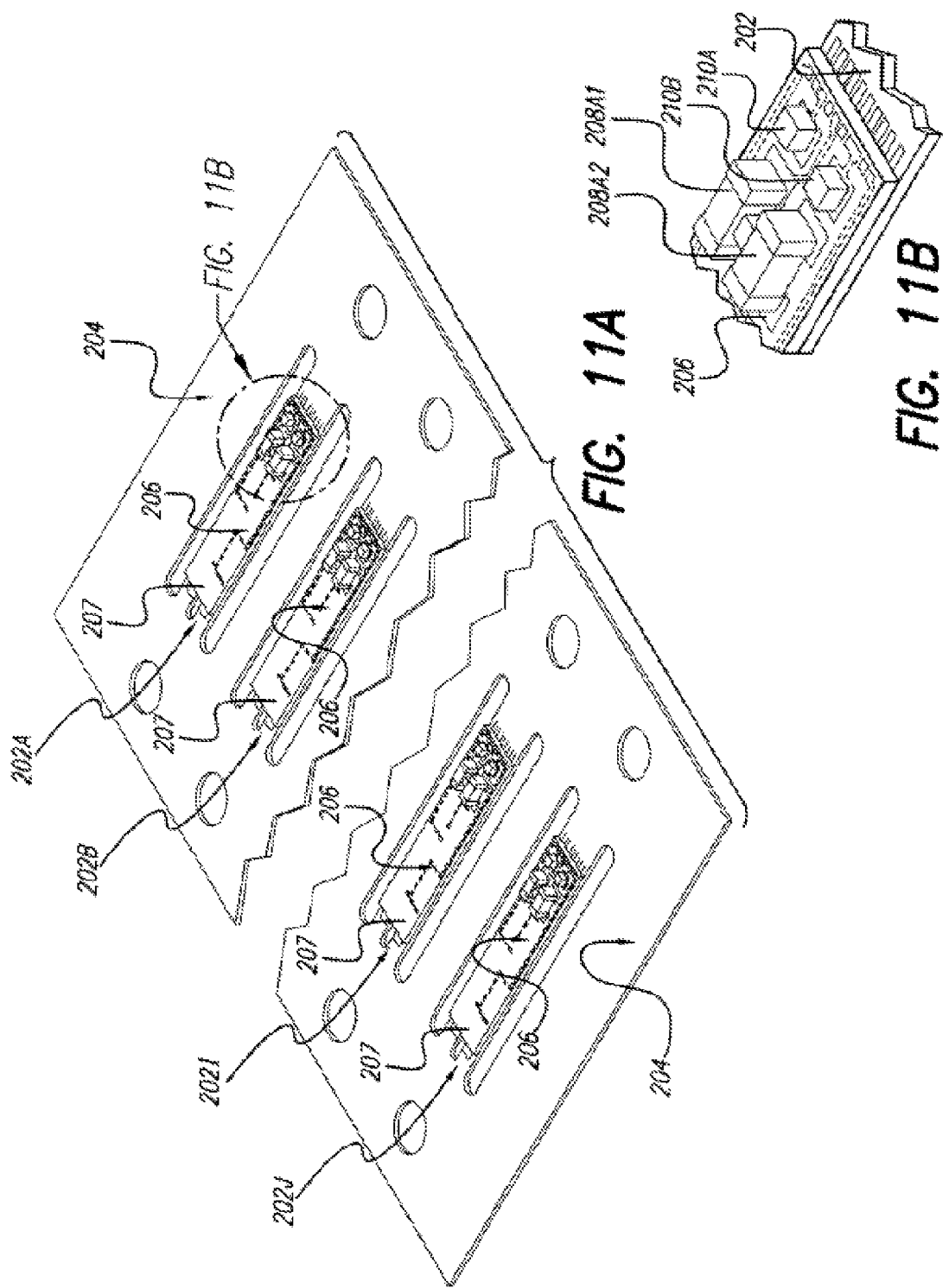
FIG. 11A is a perspective top view of the panel shown in FIG. 9 with the integrated circuitry shown in FIG. 10 and with the top capacitors and diodes attached.
FIG. 11B is an enlarged detailed view of a portion of FIG. 11A, showing in greater detail the attachment of the top capacitors and diodes.

Using the top surface 204 of the substrate assembly 202 or each substrate panel 202n, a non-conductive epoxy is applied to attach each integrated circuit 206 as shown in FIG. 10. After the ICs 206 are assembled to substrates panels 202n, each non-serialized IC 206 is now uniquely identified by the serial number laser engraved on the backside of substrate panels 202n, and can be tested and calibrated with calibration information saved together with the serial number.

Figure 12:
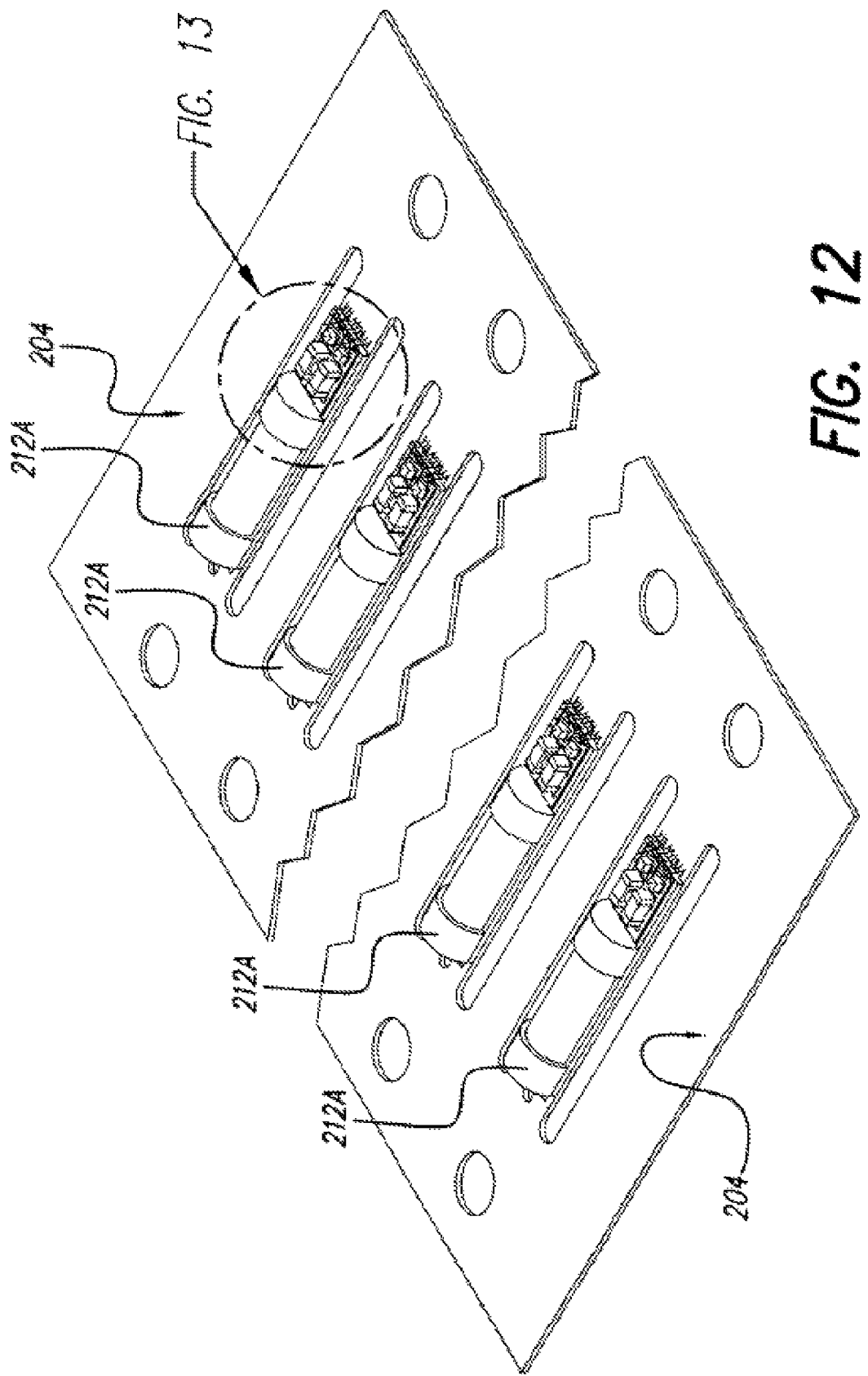
FIG. 12 is a perspective top view of the panel shown in FIG. 9 with the integrated circuitry shown in FIG. 10, the top capacitors and diodes shown in FIG. 11A, and with the top ferrite half attached.

Conductive epoxy is applied to portions of the top surface 207 of each IC 206 to mount, e.g., ceramic, capacitors 208A1 and 208A2, and the diodes 210A and 210B to their respective redistributed interconnection pads, as shown in FIG. 13. Non-conductive epoxy is applied to a portion of surface 207 of the ICs 206 to attach the top ferrite half 212A, as shown in FIG. 12. Electrical wires 214 are bonded, connecting traces on panel 202n to diodes 210A and 210B, and connecting traces on panel 202n to IC 206. An enlarged detail view of the bonded wires 214 is shown in FIG. 13. Quality inspection can be done after this step, as well as other steps in the manufacturing process.

Figure 14A:
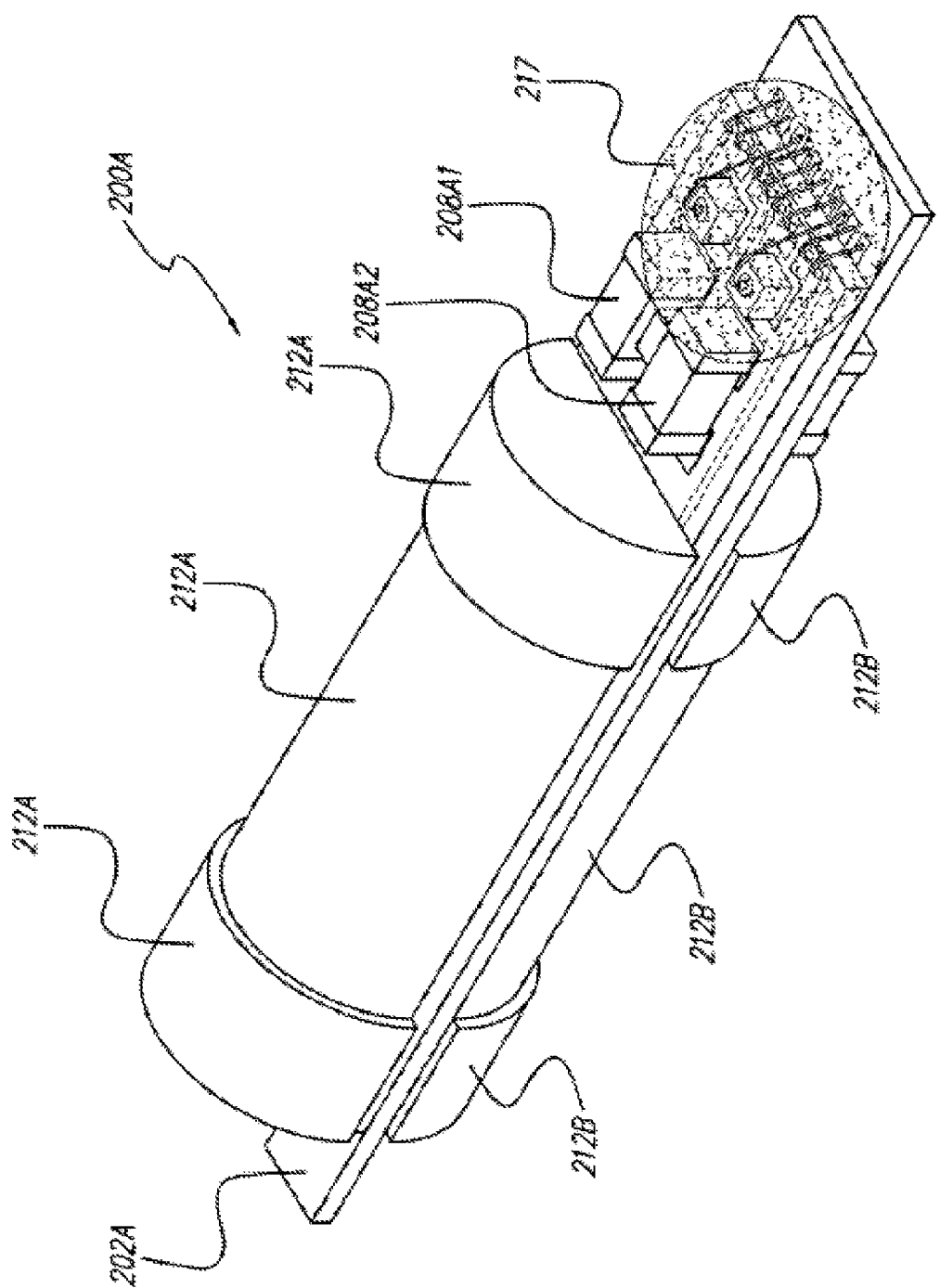
FIG. 14A is a perspective top view of a sub-assembly assembled during the manufacturing operation.

To protect the electrical wires 214 from any damage that may occur during the assembly process and handling, they may be encapsulated with an epoxyjoint 217, as shown in FIG. 14A. The mounting of the components on the top surface of the substrate panel 202 is now complete.

Figure 14B:
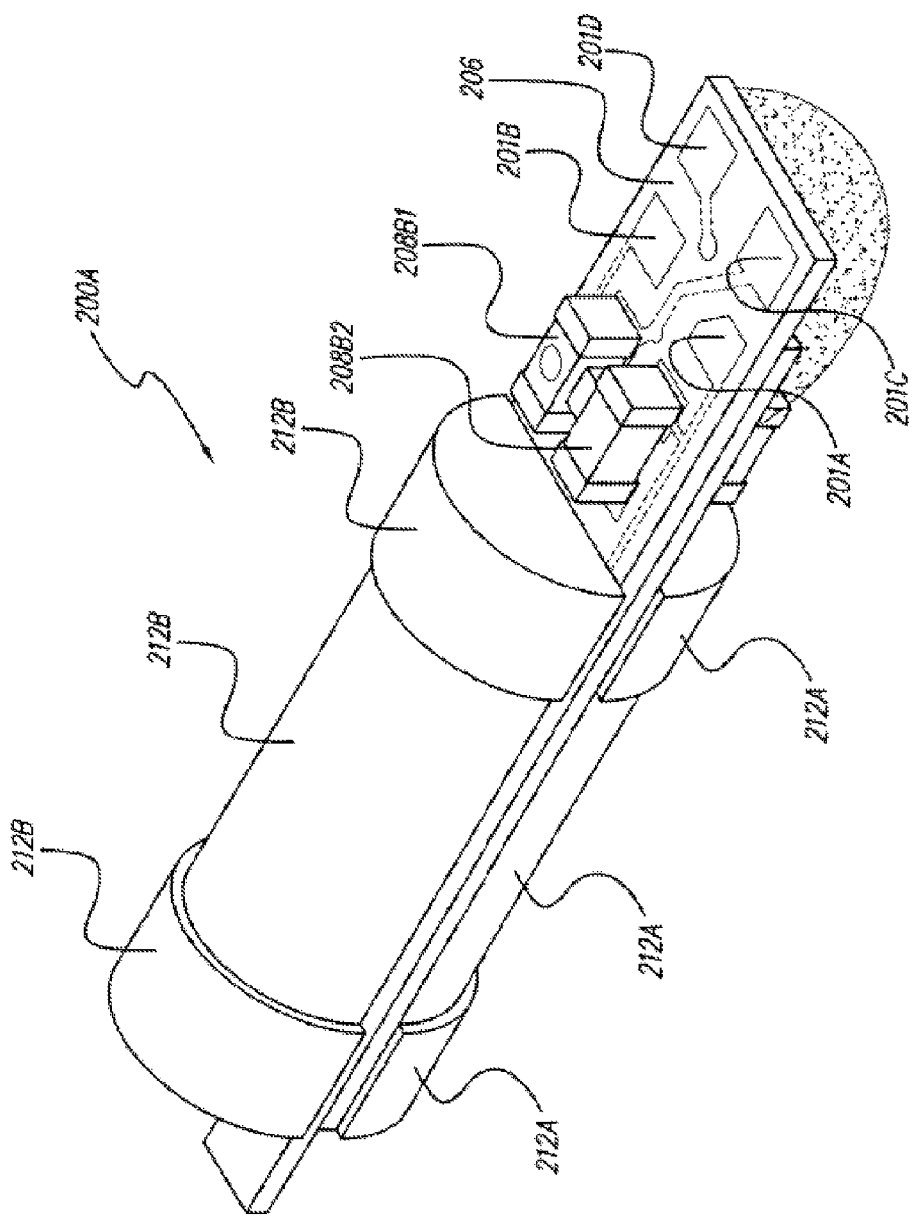
FIG. 14B is a bottom perspective view of the sub-assembly shown in FIG. 14A.

The bottom half components of the "sandwich" ferrite arrangement are assembled next to the bottom surface 205 of the substrate panel 202n (as shown in FIG. 14B). A non-conductive epoxy is applied to the portion of the bottom surface 205 used to attach the bottom ferrite half 212B. A conductive epoxy is then applied to the portion of the bottom surface 205 of the substrate panel 202n used to attach the ceramic capacitors 208B1 and 208B2.

Figure 14C:
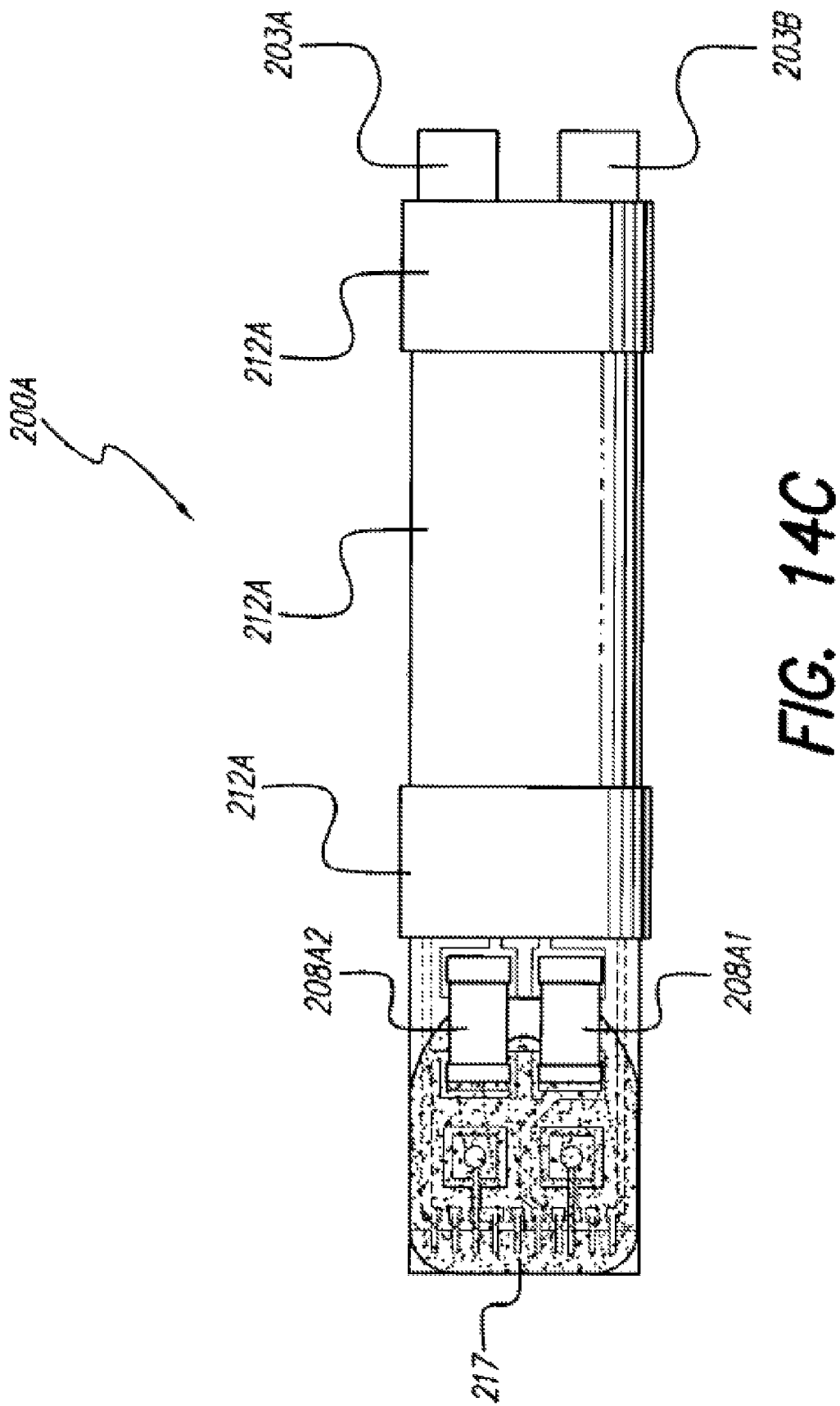
FIG. 14C is a top plan view of the sub-assembly shown in FIG. 14A.
Figure 14D:
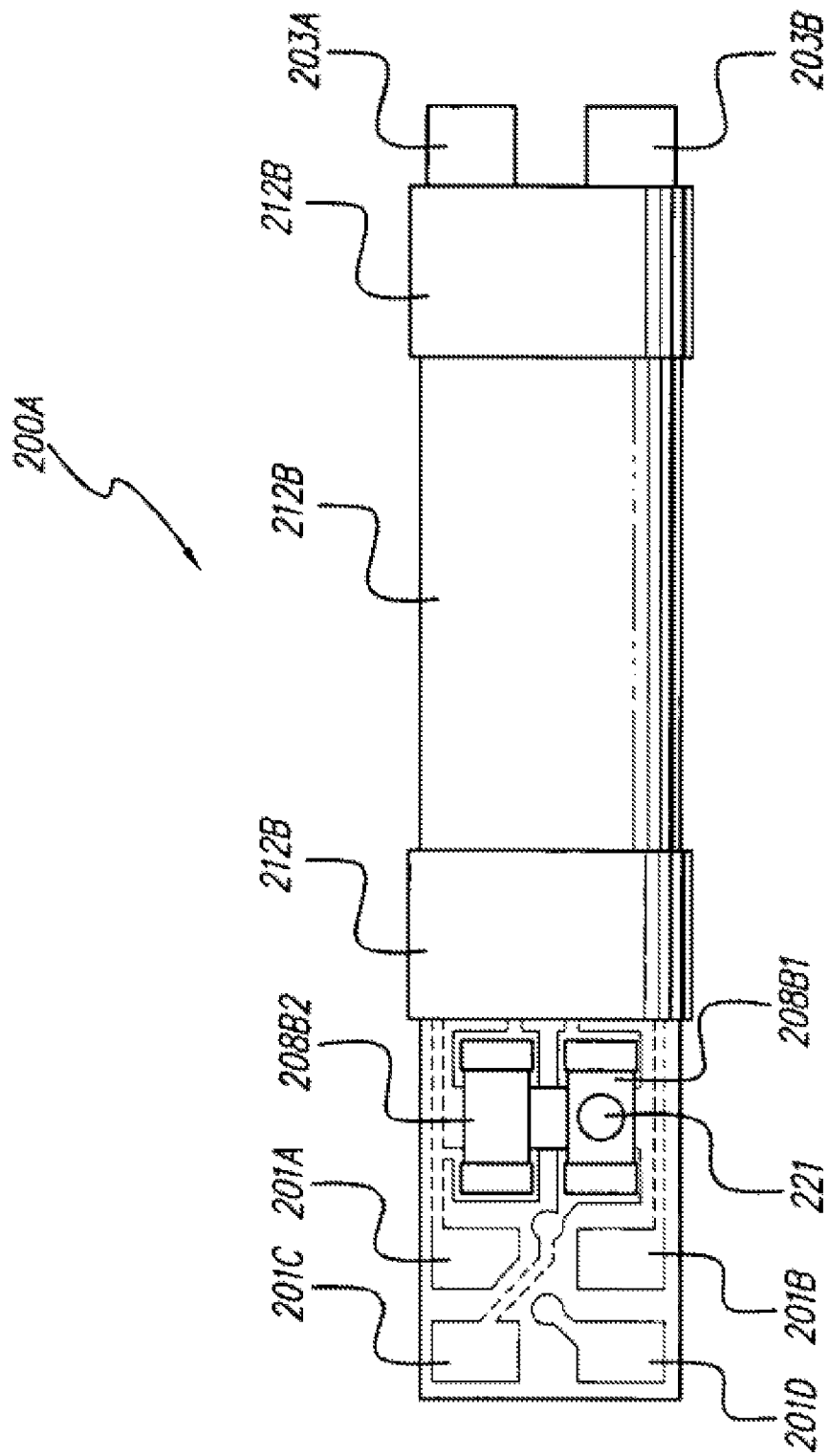
FIG. 14D is a bottom plan view of the sub-assembly shown in FIG. 14A.

The assembled units 200A are separated from panel assembly 202 by breaking away the pre-cut small portions made to contour the edge of each substrate panel 202n. FIG. 14A shows an isometric top view of a single sub-assembly 200A showing the wire bonds and diodes encapsulated in epoxy joint 217. FIG. 14B shows an isometric bottom view of the sub-assembly 200A. FIG. 14C shows the top plan view of the sub-assembly 200A showing the two pads 203A and 203B protruding from one end of the ferrite "sandwich" arrangement. The pads 203A and 203B can be used for testing the assembled electrical connections. The pads 203A and 203B are also used to connect the, e.g., tantalum, stimulating capacitor 15. FIG. 14D shows the bottom plan view of the sub-assembly 200A where the two pads 203A and 203B, as well as pads 201A, 201B, 201C, and 201D are also used for electrical test probing. The two metal pads 203C and 203D also carry the serial number. The bottom of the sub-assembly 200A is identified by the mark 221 located on the ceramic capacitor 208B1 to aid in orientation and handling during manufacturing.

Figure 15A:
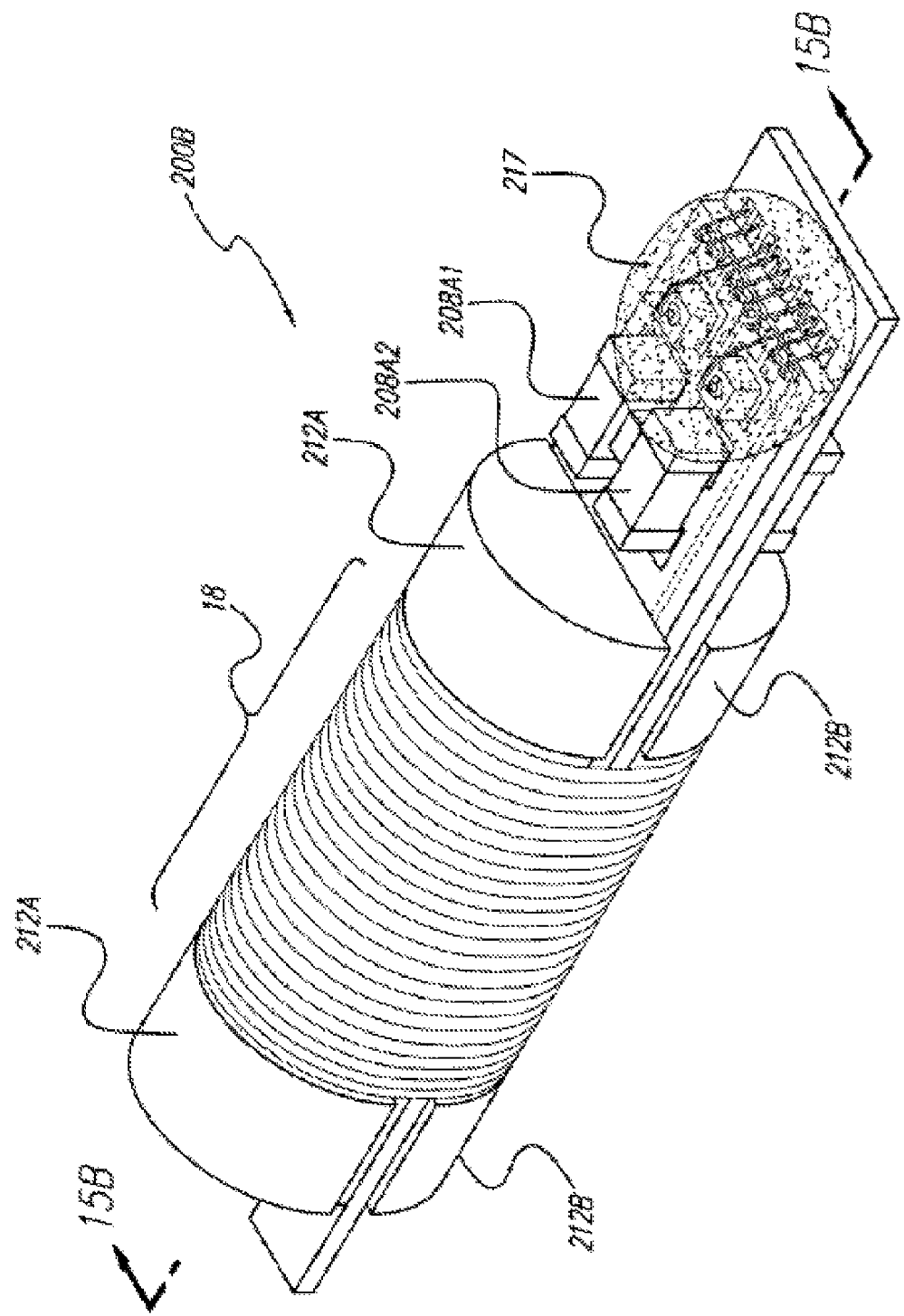
FIG. 15A is a perspective top view of the sub-assembly shown in FIG. 14A with a coil wound on the middle section of the ferrite cylinder.
Figure 15B:
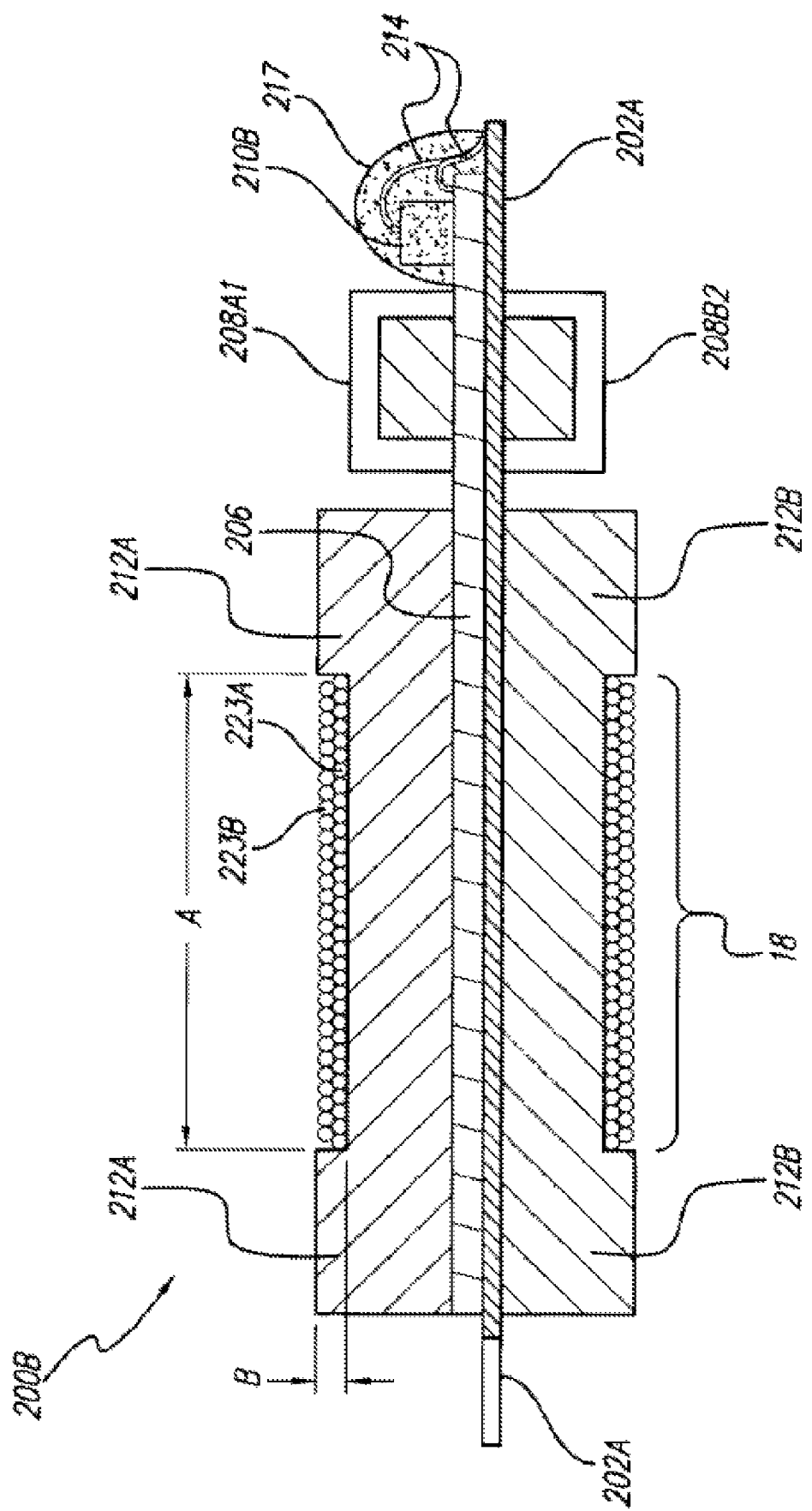
FIG. 15B is a cross-section view of the sub-assembly shown in FIG. 15A taken along line 15B-15B.

The unwound coil wire 216, made of 46 gauge insulated magnetic copper wire or other suitable conductive wire material, is then wound on the middle section of the ferrite cylinder, as shown in FIG. 15A. The coil wire 216 in a wound configuration is referred to as the BPB coil 18, as shown in FIGS. 1, 15A, and 15B. In this particular assembly process, the coil 18 has 156 turns and is wound in two layers identified as coil layer 223A and coil layer 223B, as shown in FIG. 15B, which depicts a cross-section of the sub-assembly 200B (which is the designation given to sub-assembly 200A after it has proceeded through the coil winding process). One coil layer or more than two coil layers may also be used. The required amount of layers depends on the frequency, current, and voltage requirements. Distance A (shown in FIG. 15B) is determined by the required number of coil turns and distance B (also shown in FIG. 15B) is the amount of chamfer depth required to fit the number of layers. For this application, two layers are shown in FIG. 15B. Minimizing the coil layers, which minimizes the diameter of the coil, allows subassembly 200B to fit in the smallest shell possible, for which a ceramic or other suitable material can be used. As shown in FIG. 15B, an exemplary "dumbbell" configuration is formed with the arrangement of the two ferrite halves 212A and 212B in which the gap formed by the distances A and B is used to wind the coil 216.

Figure 15C:
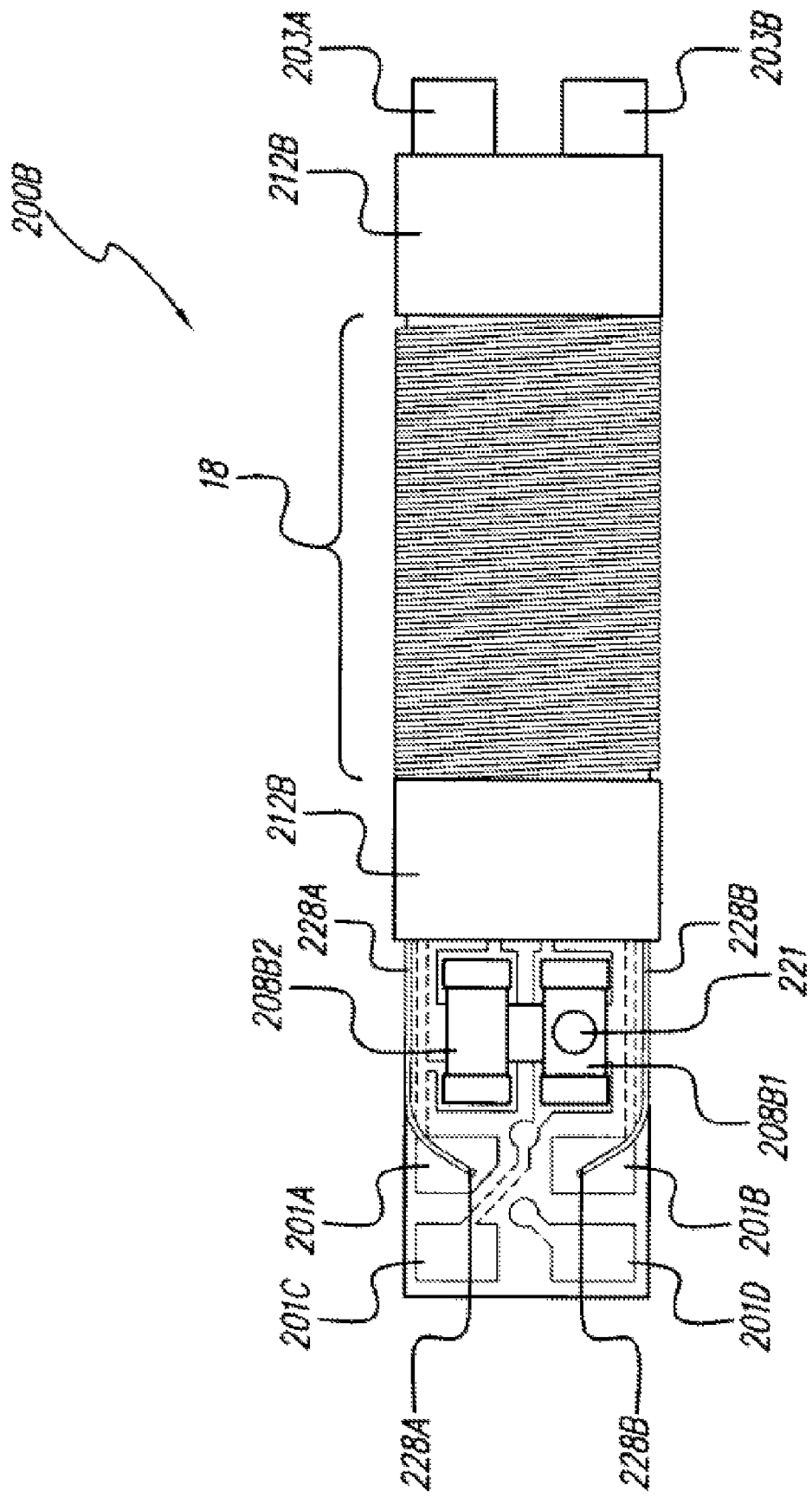
FIG. 15C is a top view of the sub-assembly shown in FIG. 14A with the coil ends depicted.
Figure 16:
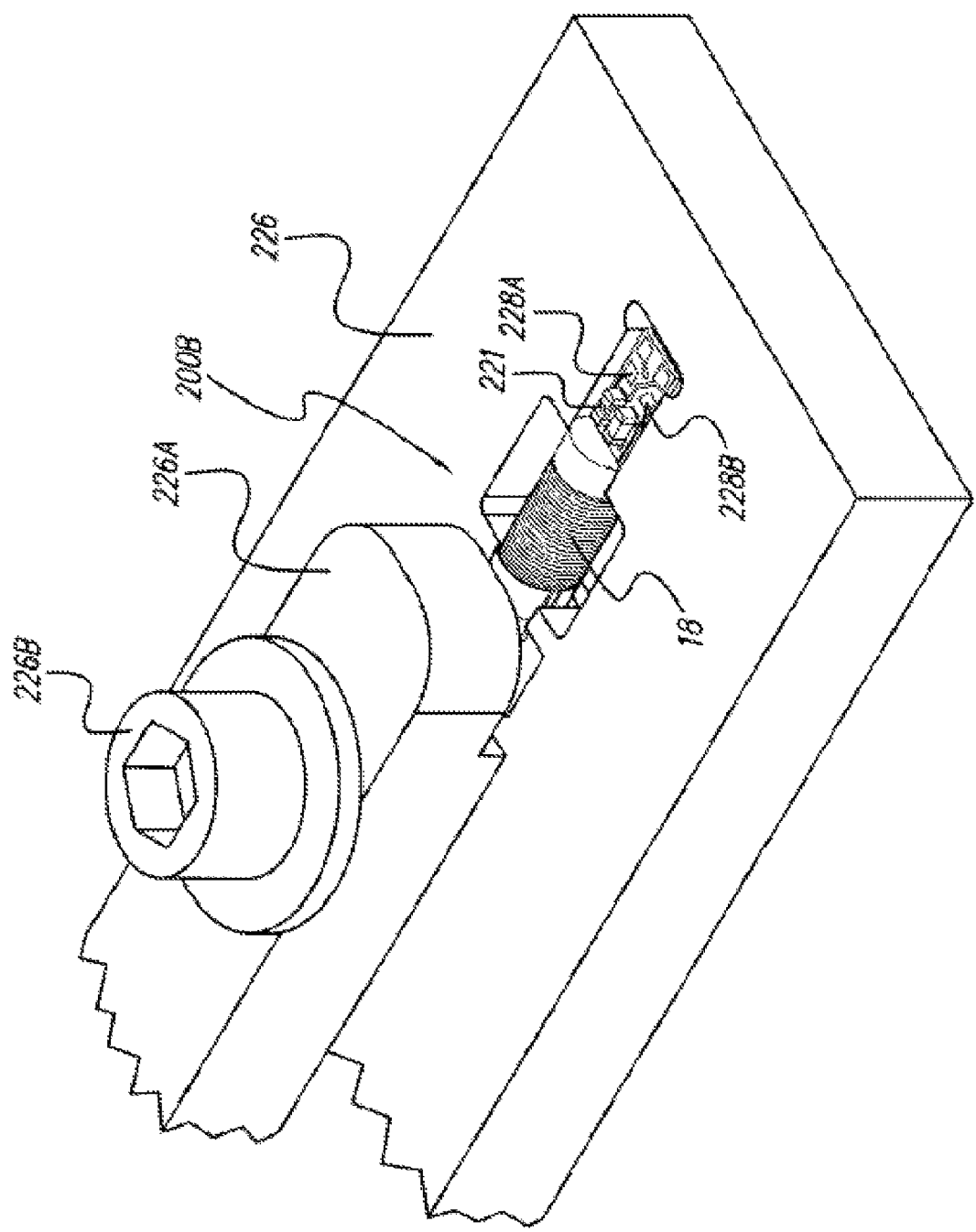
FIG. 16 is an enlarged detail perspective view of the sub-assembly shown in FIG. 15A placed in a soldering fixture.
Figure 17:
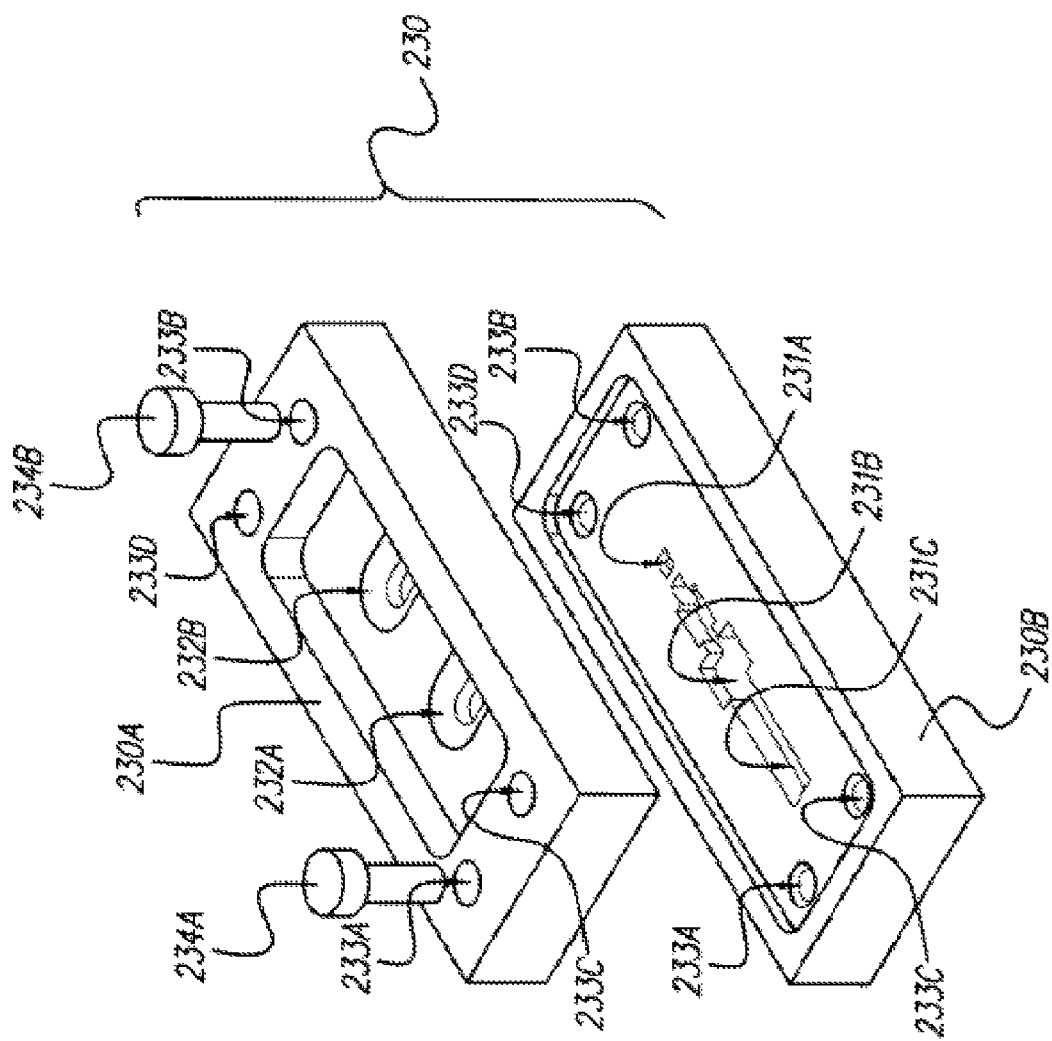
FIG. 17 is an exploded view of carrier fixture plates.

A soldering fixture 226, shown in FIG. 16, is used to assist in terminating the coil ends 228A and 228B to pads 201A and 201B of the panel 202n, as shown in FIG. 15C. Soldering the coil ends 228A and 228B becomes more practical when the sub-assembly 224 is isolated and secured using soldering fixture 226 or other similar soldering fixture. The bottom surface of the panel 202 is facing up using the mark 221 to identify this surface. The sub-assembly 200B is placed in fixture 226 with its bottom side facing up and is held firmly in place by handle 226A which is tightened by bolt 226B. FIG. 16 shows the sub-assembly 200B securely loaded in soldering fixture 226. The two coil ends, 228A and 228B, are soldered to the pads 201A and 201B (the ones next to the ceramic capacitors 208B1 and 208B2 located on the bottom surface of panel 202), as shown in FIG. 15C. This step finalizes the first assembly stage after which sub-assembly 200B is complete.

With reference to FIGS. 17-19 and 21, the second assembly stage will be described. A carrier 230, shown in FIG. 17, has been designed to facilitate the second assembly stage and aid in alignment of components. The carrier 230 consists of two plates, top plate 230A and bottom plate 230B. When plates 230A and 230B are bolted together, the machined features, 231A, 231B, and 231C securely hold the components assembled in the first operation described above. The top plate 230A also contains openings 232A, 232B, and 232C to allow access to the assembled components for processing, testing, and inspection. Two bolts 234A and 234B, aligned with holes 233A and 233B, are required to securely fasten plates 230A and 230B. Holes 233C and 233D are used to secure the assembled carrier 230 on a metal work plate 239 using pins 237A and 237B (shown in FIG. 18). Having the carrier 230 secured on the work plate 239 facilitates in a smooth assembly process.

Figure 18:
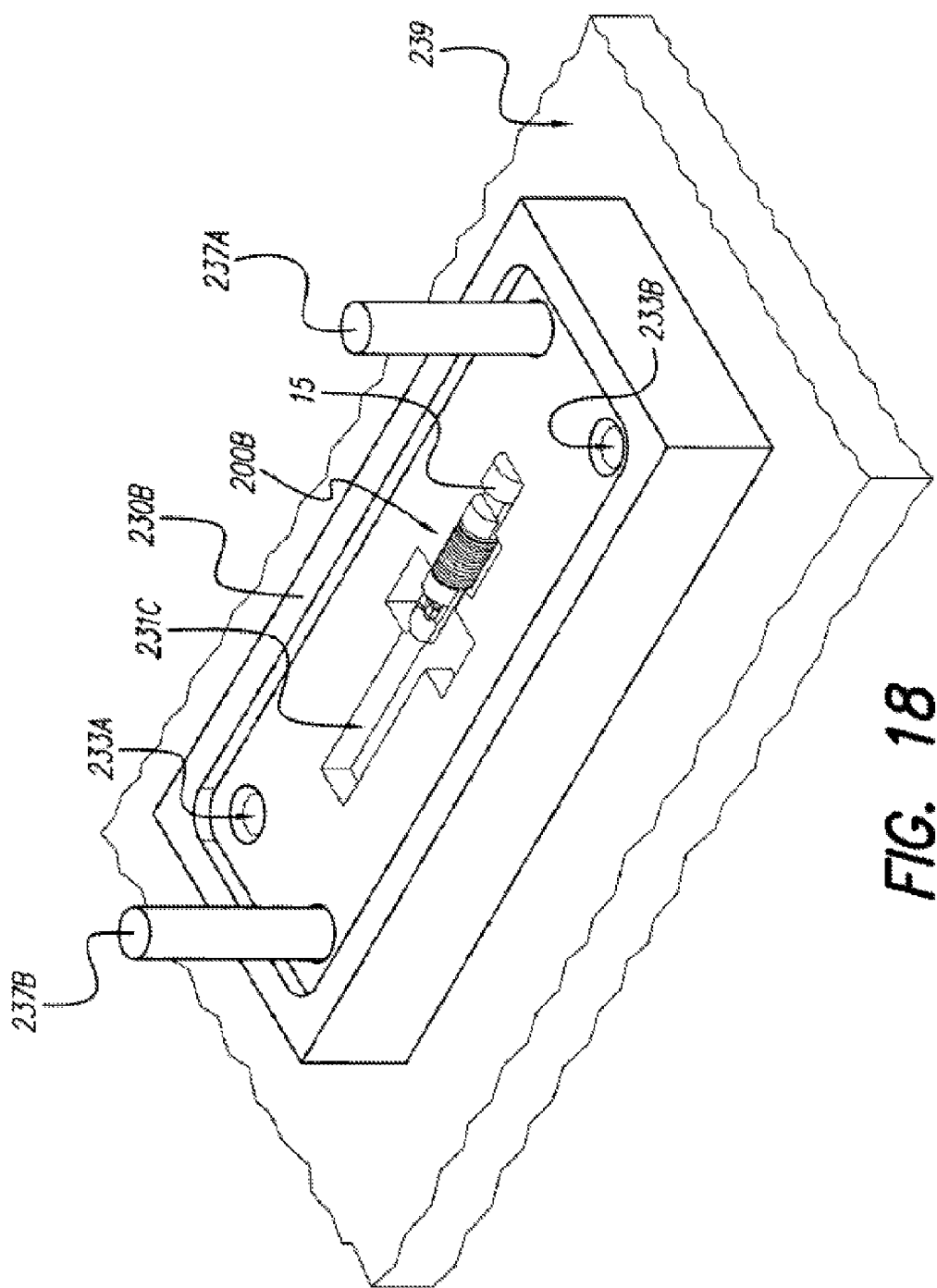
FIG. 18 is a perspective view of a supporting work-plate with one of the carrier plates shown in FIG. 17 and the sub-assembly shown in FIG. 15A.

The sub-assembly 200B and the stimulating capacitor 15 are placed in the carrier bottom plate 230B as shown in FIG. 18, then top plate 230A is bolted to bottom plate 230B with bolts 234A and 234B. Through groove opening 232B on top plate 230A, conductive epoxy 229 is applied to bond the gold-coated nickel ribbon attached to one end of the capacitor 15 to bond to pads 203A and/or 203B (seen best in FIGS. 14C and 14D). At this point, while in the carrier 230, the assembly is tested (as it is throughout the manufacturing process) and is also processed through baking temperature cycling.

Figure 19:
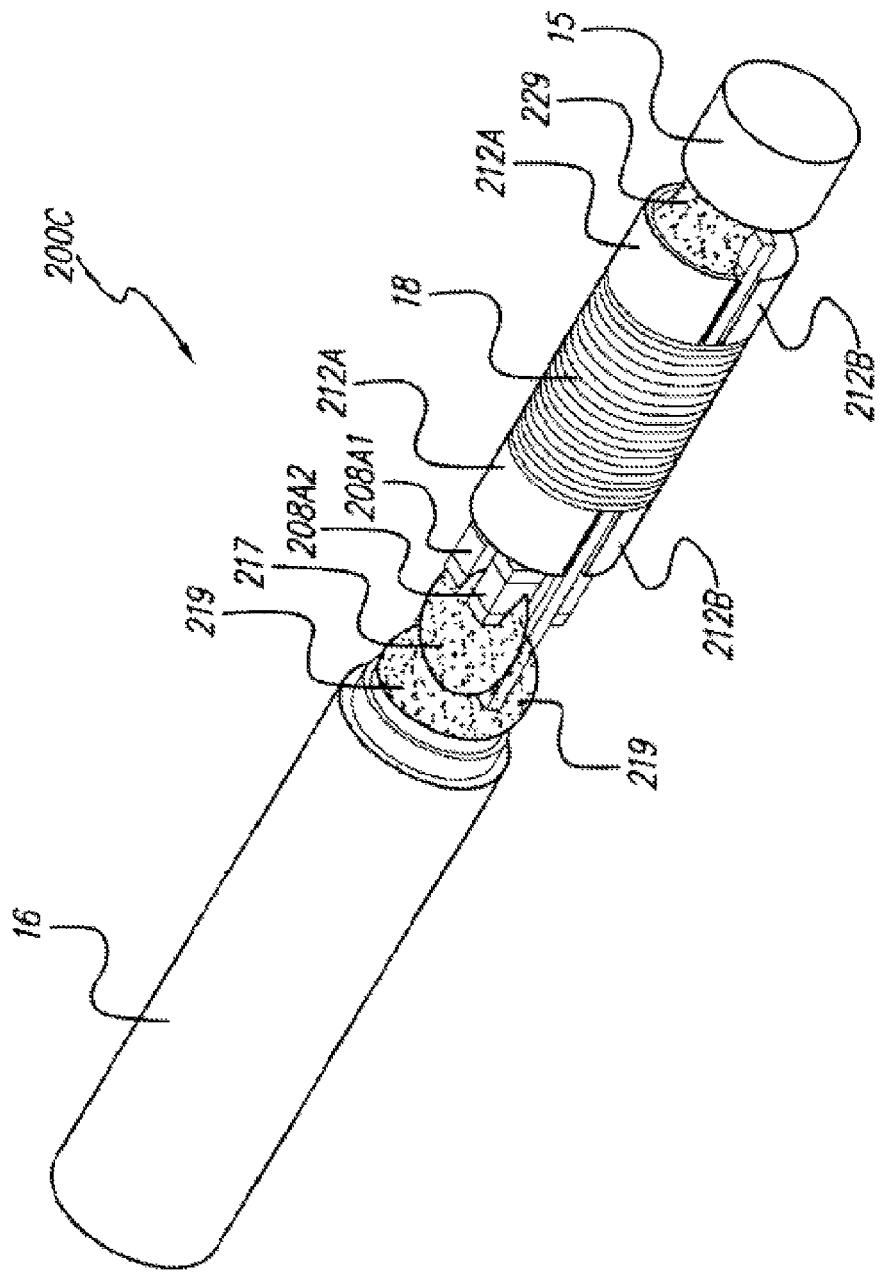
FIG. 19 is a perspective view of the sub-assembly shown in FIG. 15A with a battery attached and also depicting assembled internal components of a BPB device of the present invention.

The top carrier plate 230A is removed, the battery 16 is securely placed in the carrier groove 231C of bottom plate 230B, then top plate 230A is bolted back in place. The battery 16 has two nickel wires 68A and 68B (shown in FIG. 5) which have been pre-welded. Battery 16 is placed into groove 231C so the nickel wires 68A and 68B protrude towards the bottom surface 205 of the substrate panel 202n. Using groove opening 232B, where the nickel wires 68A and 68B of the battery 16 and the assembly 200B come together, an amount of non-conductive epoxy 219 is applied so that the ends of wires 68A and 68B are still accessible. The nickel wires 68A and 68B are bent towards and soldered to the substrate pads 201C and 201D. Additional non-conductive epoxy 219 is applied to secure the connection between the soldered nickel wires 68A and 68B and pads 201C and 201D. This finalizes the second assembly stage when the sub-assembly 200C as shown in FIG. 19 is complete.

Figure 20A:
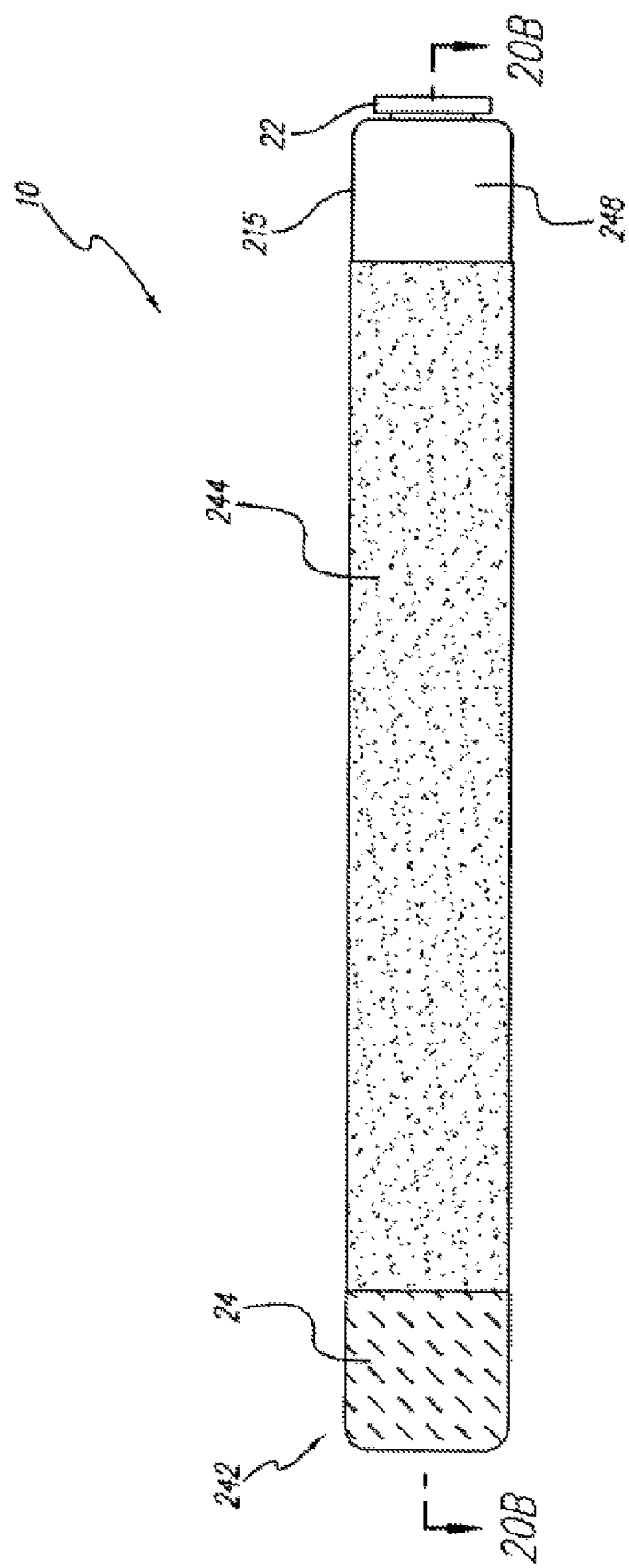
FIG. 20A is a top view of a BPB device of the present invention showing external coatings.
Figure 20B:
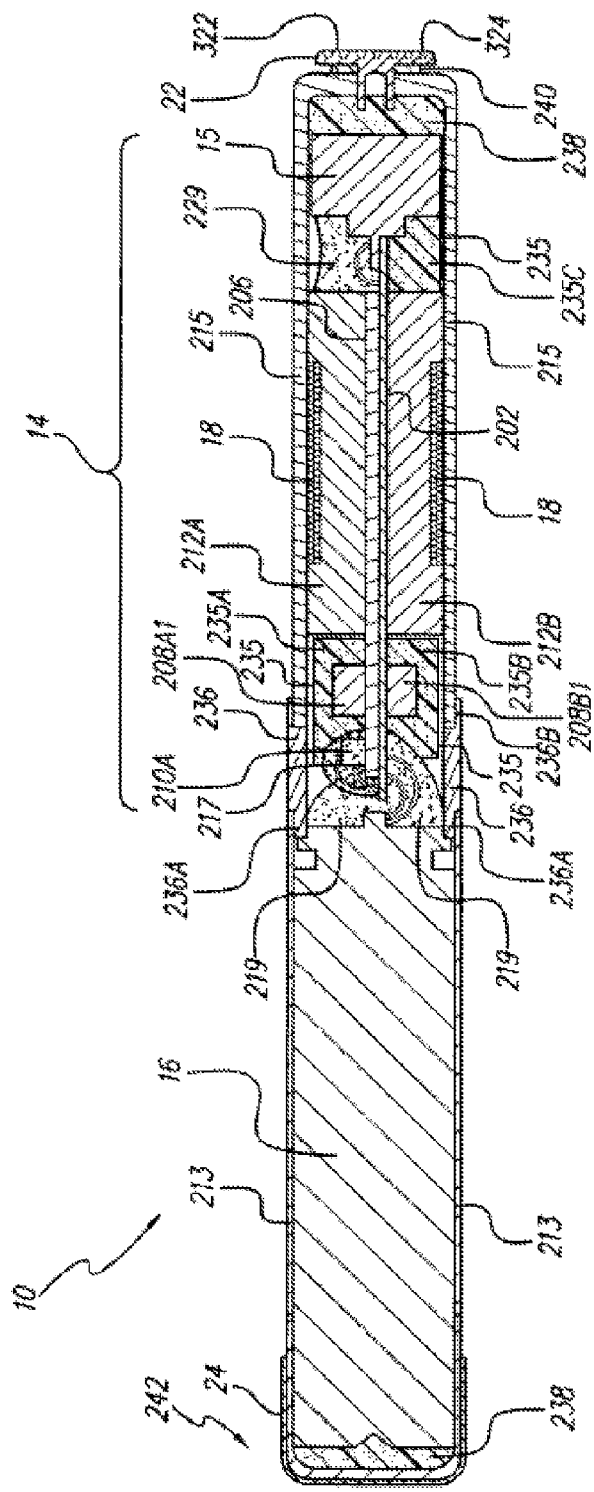
FIG. 20B is a cross-sectional view taken along line 20B-20B shown in FIG. 20A.

With reference to FIGS. 20A, 20B, 20C, and 21 the third assembly stage will be described. The assembly 200C is encapsulated within an exemplary hermetically-sealed housing which consists of, for instance, two cylindrical cases, a titanium 6/4 case 213 and a zirconia ceramic case 215, as best seen in the cross sectional view FIG. 20B. Alternative materials and shapes for the housing may also be used. A titanium 6/4 or other suitable connector 236 is brazed with a titanium nickel alloy (or other suitable material) to the ceramic case 215 for securing the mating end of the titanium case 213. The connector 236 has an inside flange 236A and an outside flange 236B which serve to "self center" the braze assembly. Before inserting the subassembly 200C and before securing the mating ends, conductive silicone adhesive 238 is applied to the inside end of the ceramic shell as well as to the inside end of the titanium shell. A molecular sieve moisture getter material 235 is also added to areas 235A, 235B, and 235C as shown in FIG. 20B before the brazing process.

Figure 20C:
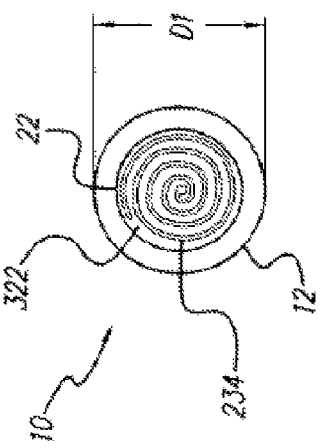
FIG. 20C is an end view of the BPB device shown in FIG. 20A.

The "spiral" self centering button electrode 22 is made from titanium 6/4 or other suitable material and is plated with an iridium coating or other suitable conductive coating. An end view of electrode 22 is shown in FIG. 20C. A spiral groove 324 is made to stimulating surface 322 of the electrode 22. The spiral groove 324 is just one example of groove shapes that may be used; other shapes, such as a cross hatch pattern or other pattern may also/instead be used. Groove 324 increases the conductive surface area 322 of electrode 22.

The sharp edges in groove 324 force a more homogeneous current distribution over the surface 322 and decrease the chances of electrode corrosion over time. The corrosion effect which may affect the electrode 22 is also known as biofouling, which is the gradual accumulation of bacteria on the surface of the electrode 22 once immersed in body fluid. When current is injected into body fluids, an electro chemical reaction occurs, producing large amounts of current density, which can contribute to the accumulation of bacteria. The spiral groove 324 or similar groove helps reduce the current density along the sharp groove edges. A tool made in the shape of a trapezoid or similar shape is used to cut the groove 324 into a spiral or other shape. Other methods of cutting the groove 324 may be used, e.g., ion beam etching.

The button electrode 22 becomes the active or stimulating electrode. A titanium/nickel alloy 240 or other suitable material is used to braze the button electrode 22 to the zirconia ceramic case 215. An end view of the BPB device 10 is shown in FIG. 20C where the end view of the stimulating "spiral" button electrode 22 can be seen. The end 242 of the titanium shell 213 is plated with an iridium coating (other suitable conductive coating may be applied), which plated area becomes the indifferent iridium electrode 24, as shown in FIG. 20A.

FIG. 20A shows a top view of the assembled BPB device 10 with the external coatings depicted. A type C parylene or other suitable insulation coating is applied to the shaded area 244, e.g., by standard masking and vapor deposition processes. The zirconia ceramic case is left exposed in area 248 and the iridium electrode 24 is shown on the end 242 of the titanium case 213. This step completes the assembly process of the BPB device 10. A cross-section of the final assembled BPB device 10 is shown in FIG. 20B.

U.S. Pat. No. 6,582,441, incorporated herein by reference, describes a surgical insertion tool which may be used for implanting the BPB device taught in this invention. The procedures taught in the '441 patent for using the tool and associated components may be used for implanting and extracting the BPB device 10 taught in the present invention. The surgical insertion tool described in the '441 patent facilitates the implantation of the BPB device in a patient such that the stimulating electrode 22 is in very close proximity to the stimulating nerve site (e.g., near the pudendal nerve for treating patients with urinary urge incontinence). The proximity range may be, for example, less than 1-2 mm.

Other implantation procedures exist relating to the specific area to be stimulated. The implantable BPB device 10 may also be implanted in other nerve sites relating to preventing and/or treating various disorders associated with, e.g., prolonged inactivity, confinement or immobilization of one or more muscles and/or as therapy for various purposes including paralyzed muscles and limbs, by providing stimulation of the cavernous nerve(s) for an effective therapy for erectile or other sexual dysfunctions, and/or by treating other disorders, e.g., neurological disorders caused by injury or stroke.

When the power source used within the BPB device is something other than a rechargeable battery, e.g., a primary battery and/or one of the alternative power sources described previously, then the circuitry within the electronic subassembly 14 (FIG. 1) is modified appropriately to interface with, control and/or monitor the particular power source that is used. For example, when the power source comprises a primary battery, the circuitry within the electronic subassembly may be simplified to include only monitoring circuitry, not charging circuitry. Such monitoring circuitry may provide status information regarding how much energy remains stored within the primary battery, thereby providing the physician and/or patient an indication relative to the remaining life of the battery.

When the power source used within the BPB device is a super capacitor, then such super capacitor will typically be used in combination with a primary battery and/or a rechargeable battery. When used in combination with a primary battery, for example, the circuitry within the electronic subassembly is modified appropriately so that the charge stored on the super capacitor is available to help power the BPB device during times of peak power demand, such as during those times when telemetry signals are being transmitted from the implanted device to the external device(s), or when the amplitude of the stimulation pulses has been programmed to be very high. When used in combination with a rechargeable battery, the circuitry within the electronic subassembly is modified appropriately so that the charge stored on the super capacitor is available to help recharge the rechargeable battery or to help power the BPB device at times of high power demand.

While the invention herein disclosed has been described by means of specific embodiments and applications thereof, numerous modifications and variations could be made thereto by those skilled in the art without departing from the scope of the invention set forth in the claims.

What is claimed is:

1. A neurostimulator system, comprising:
   a remote control;
   a base station; and
   an implantable microstimulator, wherein the microstimulator generates stimulation pulses in accordance with programmed parameters;
   wherein the remote control communicates with the microstimulator via a first telemetry link; and
   wherein the base station communicates with the implantable microstimulator via a second telemetry link, wherein power for operating the microstimulator is transferred via the second telemetry link; and
   wherein the remote control unit and base station communicate with each other via a third telemetry link.

2. The neurostimulator system of claim 1, wherein data is communicated through the first telemetry link in accordance with a frequency shift key modulation scheme.

3. The neurostimulator system of claim 1, wherein the first telemetry link comprises a radio frequency link.

4. The neurostimulator system of claim 1, wherein the base station includes a coil for producing the power.

5. The neurostimulator system of claim 1, wherein the second telemetry link further transfers information.

6. The neurostimulator system of claim 5, wherein the information is communicated through the second telemetry link in accordance with an On-Off-Key Pulse Width Modulation scheme.

7. The neurostimulator system of claim 1, wherein the first telemetry link comprises a radio frequency telemetry link, and wherein the second telemetry link comprises an electromagnetic inductive telemetry link.

8. The neurostimulator system of claim 1, wherein second telemetry link comprises either a radio frequency link or a electromagnetic inductive link.

9. The neurostimulator system of claim 1, further comprising a clinician's programmer for wirelessly communicating with the base station and the remote control.

10. The neurostimulator system of claim 1, wherein the implantable microstimulator comprises:
    an hermetically-sealed housing;
    first and second electrodes external to the hermetically-sealed housing; and
    telemetry circuitry for receiving the first and second telemetry links.

11. The neurostimulator system of claim 10, wherein the implantable microstimulator further comprises a power source within the hermetically-sealed housing which is charged by the power transferred via the second telemetry link.

12. The neurostimulator system of claim 1, wherein the first and second telemetry links are bi-directional.

13. The neurostimulator system of claim 1, wherein the third telemetry link comprises an infra-red link.

* * * * *